(12) United States Patent
Messenger et al.

(10) Patent No.: US 9,370,320 B2
(45) Date of Patent: Jun. 21, 2016

(54) METHODS, SYSTEMS AND DEVICES FOR LINKING USER DEVICES TO ACTIVITY TRACKING DEVICES

(71) Applicant: Fitbit, Inc., San Francisco, CA (US)

(72) Inventors: Jayson Messenger, San Francisco, CA (US); Barry Burton, San Francisco, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 80 days.

(21) Appl. No.: 14/265,320

(22) Filed: Apr. 29, 2014

(65) Prior Publication Data

US 2014/0236538 A1    Aug. 21, 2014

Related U.S. Application Data

(60) Continuation of application No. 14/092,864, filed on Nov. 27, 2013, now Pat. No. 8,805,646, which is a continuation-in-part of application No. 13/959,714, filed on Aug. 5, 2013, now Pat. No. 8,762,101, which (Continued)

(51) Int. Cl.
*G06F 19/00* (2011.01)
*A61B 5/11* (2006.01)
(Continued)

(52) U.S. Cl.
CPC ............. *A61B 5/1118* (2013.01); *A61B 5/0022* (2013.01); *A63B 24/0062* (2013.01); *A63B 71/0686* (2013.01); *G01C 22/00* (2013.01);
(Continued)

(58) Field of Classification Search
CPC ..... G06F 19/3418; G06Q 10/02; G06Q 50/22

USPC .......................... 702/160, 150, 182–185, 188
See application file for complete search history.

(56) References Cited

U.S. PATENT DOCUMENTS 2,284,849 A   8/1941  Anderson et al.
2,717,736 A   9/1955  Schlesinger
(Continued)

FOREIGN PATENT DOCUMENTS

JP          11347021       12/1999
WO   WO 2008/038141     4/2008
WO   WO 2009/042965     4/2009

OTHER PUBLICATIONS

Deepak et al., Plug-and-Play, Single-Chip Photoplethysmography, 34th Annual International Conference of the IEEE EMBS, San Diego, California USA, Aug. 28-Sep. 1, 2012, 4 pages.

(Continued)

*Primary Examiner* — Edward Raymond
(74) *Attorney, Agent, or Firm* — Martine Penilla Group, LLP

(57) ABSTRACT

Methods, systems and devices for linking devices to tracking devices is provided. One method includes scanning, by an activity tracking device, for a semi-unique identifier broadcasted by a device. The method connects the device with the activity tracking device after the semi-unique identifier is found to be of the device by the activity tracking device. The activity tracking device is configured to communicate with the device to obtain a device identification (ID) of the device. The method then automatically linking the device to the activity tracking device when the device ID of the device matches a copy of the device ID stored in the activity tracking device. In one example, the tracking devices operate as a master and the devices operate as a slave.

20 Claims, 10 Drawing Sheets

Related U.S. Application Data is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 13/959,714, which is a continuation-in-part of application No. 13/759,485, filed on Feb. 5, 2013, now Pat. No. 8,543,351, which is a division of application No. 13/667,229.

(60) Provisional application No. 61/388,595, filed on Sep. 30, 2010, provisional application No. 61/390,811, filed on Oct. 7, 2010.

(51) Int. Cl.
| | |
|---|---|
| *G01P 13/00* | (2006.01) |
| *G01C 22/00* | (2006.01) |
| *G06F 15/00* | (2006.01) |
| *A63B 24/00* | (2006.01) |
| *A63B 71/06* | (2006.01) |
| *A61B 5/00* | (2006.01) |
| *A61B 5/0205* | (2006.01) |
| *A61B 5/021* | (2006.01) |
| *A61B 5/024* | (2006.01) |
| *A61B 5/22* | (2006.01) |

(52) U.S. Cl.
CPC .............. *G01C 22/006* (2013.01); *G01P 13/00* (2013.01); *G06F 15/00* (2013.01); *A61B 5/021* (2013.01); *A61B 5/024* (2013.01); *A61B 5/02055* (2013.01); *A61B 5/1112* (2013.01); *A61B 5/222* (2013.01); *A61B 5/4809* (2013.01); *A61B 5/4812* (2013.01); *A61B 5/4815* (2013.01); *A61B 5/6838* (2013.01); *A61B 2560/0214* (2013.01); *A61B 2560/0242* (2013.01); *A61B 2560/0271* (2013.01); *A61B 2562/0219* (2013.01); *A63B 2220/73* (2013.01); *A63B 2230/06* (2013.01); *A63B 2230/50* (2013.01); *A63B 2230/70* (2013.01); *A63B 2230/75* (2013.01); *G06F 19/3406* (2013.01); *G06F 19/3481* (2013.01)

(56) References Cited

U.S. PATENT DOCUMENTS

| | | | |
|---|---|---|---|
| 2,883,255 | A | 4/1959 | Anderson |
| 3,163,856 | A | 12/1964 | Kirby |
| 3,250,270 | A | 5/1966 | Bloom |
| 3,918,658 | A | 11/1975 | Beller |
| 4,192,000 | A | 3/1980 | Lipsey |
| 4,244,020 | A | 1/1981 | Ratcliff |
| 4,281,663 | A | 8/1981 | Pringle |
| 4,284,849 | A | 8/1981 | Anderson et al. |
| 4,312,358 | A | 1/1982 | Barney |
| 4,367,752 | A | 1/1983 | Jimenez et al. |
| 4,390,922 | A | 6/1983 | Pelliccia |
| 4,407,295 | A | 10/1983 | Steuer et al. |
| 4,425,921 | A | 1/1984 | Fujisaki et al. |
| 4,575,804 | A | 3/1986 | Ratcliff |
| 4,578,769 | A | 3/1986 | Frederick |
| 4,617,525 | A | 10/1986 | Lloyd |
| 4,887,249 | A | 12/1989 | Thinesen |
| 4,977,509 | A | 12/1990 | Pitchford et al. |
| 5,058,427 | A | 10/1991 | Brandt |
| 5,224,059 | A | 6/1993 | Nitta et al. |
| 5,295,085 | A | 3/1994 | Hoffacker |
| 5,323,650 | A | 6/1994 | Fullen et al. |
| 5,446,705 | A | 8/1995 | Haas et al. |
| 5,456,648 | A | 10/1995 | Edinburg et al. |
| 5,583,776 | A | 12/1996 | Levi et al. |
| 5,671,162 | A | 9/1997 | Werbin |
| 5,704,350 | A | 1/1998 | Williams, III |
| 5,724,265 | A | 3/1998 | Hutchings |
| 5,890,128 | A | 3/1999 | Diaz et al. |
| 5,891,042 | A | 4/1999 | Sham et al. |
| 5,894,454 | A | 4/1999 | Kondo |
| 5,899,963 | A | 5/1999 | Hutchings |
| 5,947,868 | A | 9/1999 | Dugan |
| 5,955,667 | A | 9/1999 | Fyfe |
| 5,976,083 | A | 11/1999 | Richardson et al. |
| 6,018,705 | A | 1/2000 | Gaudet et al. |
| 6,077,193 | A | 6/2000 | Buhler et al. |
| 6,085,248 | A | 7/2000 | Sambamurthy et al. |
| 6,129,686 | A | 10/2000 | Friedman |
| 6,145,389 | A | 11/2000 | Ebeling et al. |
| 6,183,425 | B1 | 2/2001 | Whalen et al. |
| 6,213,872 | B1 | 4/2001 | Harada et al. |
| 6,241,684 | B1 | 6/2001 | Amano et al. |
| 6,287,262 | B1 | 9/2001 | Amano et al. |
| 6,301,964 | B1 | 10/2001 | Fyfe et al. |
| 6,302,789 | B2 | 10/2001 | Harada et al. |
| 6,305,221 | B1 | 10/2001 | Hutchings |
| 6,309,360 | B1 | 10/2001 | Mault |
| 6,469,639 | B2 | 10/2002 | Tanenhaus et al. |
| 6,478,736 | B1 | 11/2002 | Mault |
| 6,513,381 | B2 | 2/2003 | Fyfe et al. |
| 6,513,532 | B2 | 2/2003 | Mault et al. |
| 6,527,711 | B1 | 3/2003 | Stivoric et al. |
| 6,529,827 | B1 | 3/2003 | Beason et al. |
| 6,561,951 | B2 | 5/2003 | Cannon et al. |
| 6,571,200 | B1 | 5/2003 | Mault |
| 6,585,622 | B1 | 7/2003 | Shum et al. |
| 6,607,493 | B2 | 8/2003 | Song |
| 6,620,078 | B2 | 9/2003 | Pfeffer |
| 6,678,629 | B2 | 1/2004 | Tsuji |
| 6,699,188 | B2 | 3/2004 | Wessel |
| 6,761,064 | B2 | 7/2004 | Tsuji |
| 6,790,178 | B1 | 9/2004 | Mault et al. |
| 6,808,473 | B2 | 10/2004 | Hisano et al. |
| 6,811,516 | B1 | 11/2004 | Dugan |
| 6,813,582 | B2 | 11/2004 | Levi et al. |
| 6,813,931 | B2 | 11/2004 | Yadav et al. |
| 6,856,938 | B2 | 2/2005 | Kurtz |
| 6,862,575 | B1 | 3/2005 | Anttila et al. |
| 7,062,225 | B2 | 6/2006 | White |
| 7,162,368 | B2 | 1/2007 | Levi et al. |
| 7,171,331 | B2 | 1/2007 | Vock et al. |
| 7,200,517 | B2 | 4/2007 | Darley et al. |
| 7,246,033 | B1 | 7/2007 | Kudo |
| 7,261,690 | B2 | 8/2007 | Teller et al. |
| 7,272,982 | B2 | 9/2007 | Neuhauser et al. |
| 7,373,820 | B1 | 5/2008 | James |
| 7,443,292 | B2 | 10/2008 | Jensen et al. |
| 7,457,724 | B2 | 11/2008 | Vock et al. |
| 7,467,060 | B2 | 12/2008 | Kulach et al. |
| 7,505,865 | B2 | 3/2009 | Ohkubo et al. |
| 7,559,877 | B2 | 7/2009 | Parks et al. |
| 7,653,508 | B1 | 1/2010 | Kahn et al. |
| 7,690,556 | B1 | 4/2010 | Kahn et al. |
| 7,713,173 | B2 | 5/2010 | Shin et al. |
| 7,762,952 | B2 | 7/2010 | Lee et al. |
| 7,774,156 | B2 | 8/2010 | Niva et al. |
| 7,789,802 | B2 | 9/2010 | Lee et al. |
| 7,881,902 | B1 | 2/2011 | Kahn et al. |
| 7,927,253 | B2 | 4/2011 | Vincent et al. |
| 7,983,876 | B2 | 7/2011 | Vock et al. |
| 8,028,443 | B2 | 10/2011 | Case, Jr. |
| 8,055,469 | B2 | 11/2011 | Kulach et al. |
| 8,099,318 | B2 | 1/2012 | Moukas et al. |
| 8,177,260 | B2 | 5/2012 | Tropper et al. |
| 8,180,591 | B2 | 5/2012 | Yuen et al. |
| 8,180,592 | B2 | 5/2012 | Yuen et al. |
| 8,311,769 | B2 | 11/2012 | Yuen et al. |

(56) References Cited

U.S. PATENT DOCUMENTS

| | | | |
|---|---|---|---|
| 8,311,770 B2 | 11/2012 | Yuen et al. | |
| 8,386,008 B2 | 2/2013 | Yuen et al. | |
| 8,437,980 B2 | 5/2013 | Yuen et al. | |
| 8,463,576 B2 | 6/2013 | Yuen et al. | |
| 8,463,577 B2 | 6/2013 | Yuen et al. | |
| 8,543,185 B2 | 9/2013 | Yuen et al. | |
| 8,543,351 B2 | 9/2013 | Yuen et al. | |
| 8,548,770 B2 | 10/2013 | Yuen et al. | |
| 8,583,402 B2 | 11/2013 | Yuen et al. | |
| 8,597,093 B2 | 12/2013 | Engelberg et al. | |
| 8,670,953 B2 | 3/2014 | Yuen et al. | |
| 9,047,648 B1* | 6/2015 | Lekutai | G06Q 50/22 |
| 2001/0055242 A1 | 12/2001 | Deshmuhk et al. | |
| 2002/0013717 A1 | 1/2002 | Ando et al. | |
| 2002/0077219 A1 | 6/2002 | Cohen et al. | |
| 2002/0082144 A1 | 6/2002 | Pfeffer | |
| 2002/0109600 A1 | 8/2002 | Mault et al. | |
| 2002/0178060 A1 | 11/2002 | Sheehan | |
| 2002/0198776 A1 | 12/2002 | Nara et al. | |
| 2003/0018523 A1 | 1/2003 | Rappaport et al. | |
| 2003/0050537 A1 | 3/2003 | Wessel | |
| 2003/0065561 A1 | 4/2003 | Brown et al. | |
| 2003/0131059 A1 | 7/2003 | Brown et al. | |
| 2004/0054497 A1 | 3/2004 | Kurtz | |
| 2004/0061324 A1 | 4/2004 | Howard | |
| 2004/0117963 A1 | 6/2004 | Schneider | |
| 2004/0152957 A1 | 8/2004 | Stivoric et al. | |
| 2005/0037844 A1 | 2/2005 | Shum et al. | |
| 2005/0038679 A1 | 2/2005 | Short | |
| 2005/0054938 A1 | 3/2005 | Wehman et al. | |
| 2005/0102172 A1 | 5/2005 | Sirmans, Jr. | |
| 2005/0107723 A1 | 5/2005 | Wehman et al. | |
| 2005/0228244 A1 | 10/2005 | Banet | |
| 2005/0228692 A1 | 10/2005 | Hodgdon | |
| 2005/0234742 A1 | 10/2005 | Hodgdon | |
| 2005/0248718 A1 | 11/2005 | Howell et al. | |
| 2005/0272564 A1 | 12/2005 | Pyles et al. | |
| 2006/0020177 A1 | 1/2006 | Seo et al. | |
| 2006/0025282 A1 | 2/2006 | Redmann | |
| 2006/0047208 A1 | 3/2006 | Yoon | |
| 2006/0047447 A1 | 3/2006 | Brady et al. | |
| 2006/0089542 A1 | 4/2006 | Sands | |
| 2006/0111944 A1 | 5/2006 | Sirmans, Jr. et al. | |
| 2006/0129436 A1 | 6/2006 | Short | |
| 2006/0143645 A1 | 6/2006 | Vock et al. | |
| 2006/0277474 A1 | 12/2006 | Robarts et al. | |
| 2006/0282021 A1 | 12/2006 | DeVaul et al. | |
| 2006/0287883 A1 | 12/2006 | Turgiss et al. | |
| 2007/0050715 A1 | 3/2007 | Behar | |
| 2007/0051369 A1 | 3/2007 | Choi et al. | |
| 2007/0071643 A1 | 3/2007 | Hall et al. | |
| 2007/0123391 A1 | 5/2007 | Shin et al. | |
| 2007/0136093 A1 | 6/2007 | Rankin et al. | |
| 2007/0155277 A1 | 7/2007 | Amitai et al. | |
| 2007/0159926 A1 | 7/2007 | Prstojevich et al. | |
| 2007/0179356 A1 | 8/2007 | Wessel | |
| 2007/0194066 A1 | 8/2007 | Ishihara et al. | |
| 2007/0197920 A1 | 8/2007 | Adams | |
| 2007/0208544 A1 | 9/2007 | Kulach et al. | |
| 2007/0276271 A1 | 11/2007 | Chan | |
| 2008/0093838 A1 | 4/2008 | Tropper et al. | |
| 2008/0125288 A1 | 5/2008 | Case | |
| 2008/0140163 A1 | 6/2008 | Keacher et al. | |
| 2008/0140338 A1 | 6/2008 | No et al. | |
| 2009/0018797 A1 | 1/2009 | Kasama et al. | |
| 2009/0043531 A1 | 2/2009 | Kahn et al. | |
| 2009/0048044 A1 | 2/2009 | Oleson et al. | |
| 2009/0054737 A1 | 2/2009 | Magar et al. | |
| 2009/0063193 A1 | 3/2009 | Barton et al. | |
| 2009/0063293 A1 | 3/2009 | Mirrashidi et al. | |
| 2009/0171788 A1 | 7/2009 | Tropper et al. | |
| 2009/0271147 A1 | 10/2009 | Sugai | |
| 2010/0205541 A1 | 8/2010 | Rapaport et al. | |
| 2010/0217099 A1 | 8/2010 | LeBoeuf et al. | |
| 2011/0003665 A1 | 1/2011 | Burton et al. | |
| 2011/0009051 A1 | 1/2011 | Khedouri et al. | |
| 2011/0022349 A1 | 1/2011 | Stirling et al. | |
| 2011/0080349 A1 | 4/2011 | Holbein et al. | |
| 2011/0106449 A1 | 5/2011 | Chowdhary et al. | |
| 2011/0131005 A1 | 6/2011 | Ueshima et al. | |
| 2011/0193704 A1 | 8/2011 | Harper et al. | |
| 2011/0224508 A1 | 9/2011 | Moon | |
| 2011/0230729 A1 | 9/2011 | Shirasaki et al. | |
| 2012/0072165 A1 | 3/2012 | Jallon | |
| 2012/0083705 A1 | 4/2012 | Yuen et al. | |
| 2012/0083714 A1 | 4/2012 | Yuen et al. | |
| 2012/0083715 A1 | 4/2012 | Yuen et al. | |
| 2012/0083716 A1 | 4/2012 | Yuen et al. | |
| 2012/0084053 A1 | 4/2012 | Yuen et al. | |
| 2012/0084054 A1 | 4/2012 | Yuen et al. | |
| 2012/0092157 A1 | 4/2012 | Tran | |
| 2012/0183939 A1 | 7/2012 | Aragones et al. | |
| 2012/0226471 A1 | 9/2012 | Yuen et al. | |
| 2012/0226472 A1 | 9/2012 | Yuen et al. | |
| 2012/0227737 A1 | 9/2012 | Mastrototaro et al. | |
| 2012/0265480 A1 | 10/2012 | Oshima | |
| 2012/0330109 A1 | 12/2012 | Tran | |
| 2013/0006718 A1 | 1/2013 | Nielsen et al. | |
| 2013/0072169 A1 | 3/2013 | Ross et al. | |
| 2013/0073254 A1 | 3/2013 | Yuen et al. | |
| 2013/0073255 A1 | 3/2013 | Yuen et al. | |
| 2013/0080113 A1 | 3/2013 | Yuen et al. | |
| 2013/0095459 A1 | 4/2013 | Tran | |
| 2013/0096843 A1 | 4/2013 | Yuen et al. | |
| 2013/0151196 A1 | 6/2013 | Yuen et al. | |
| 2013/0158369 A1 | 6/2013 | Yuen et al. | |
| 2013/0231574 A1 | 9/2013 | Tran | |
| 2013/0261475 A1 | 10/2013 | Mochizuki | |
| 2013/0267249 A1 | 10/2013 | Rosenberg | |
| 2013/0268199 A1 | 10/2013 | Nielsen et al. | |
| 2013/0268236 A1 | 10/2013 | Yuen et al. | |
| 2013/0296666 A1 | 11/2013 | Kumar et al. | |
| 2013/0296673 A1 | 11/2013 | Thaveeprungsriporn et al. | |
| 2013/0310896 A1 | 11/2013 | Mass | |
| 2013/0325396 A1 | 12/2013 | Yuen et al. | |
| 2014/0035761 A1 | 2/2014 | Burton et al. | |
| 2014/0039804 A1 | 2/2014 | Park et al. | |
| 2014/0039840 A1 | 2/2014 | Yuen et al. | |
| 2014/0077673 A1 | 3/2014 | Garg et al. | |

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Non-restricted measurement of walking distance", Sagawa, et al, IEEE Int'l Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

(56) References Cited

OTHER PUBLICATIONS

"Drift-free dynamic height sensor using MEMS IMU aided by MEMS pressure sensor", Tanigawa, et al, Workshop on Positioning, Navigation and Communication, Mar. 2008, pp. 191-196.

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

* cited by examiner

PAIR ACTIVITY TRACKING DEVICE TO SITE

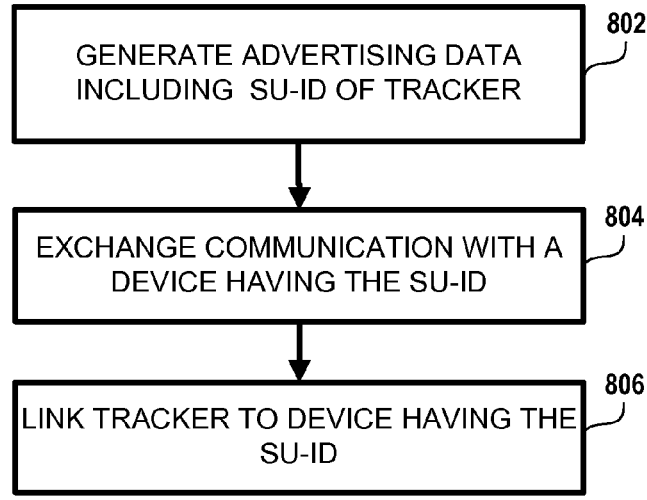
FIG. 8A
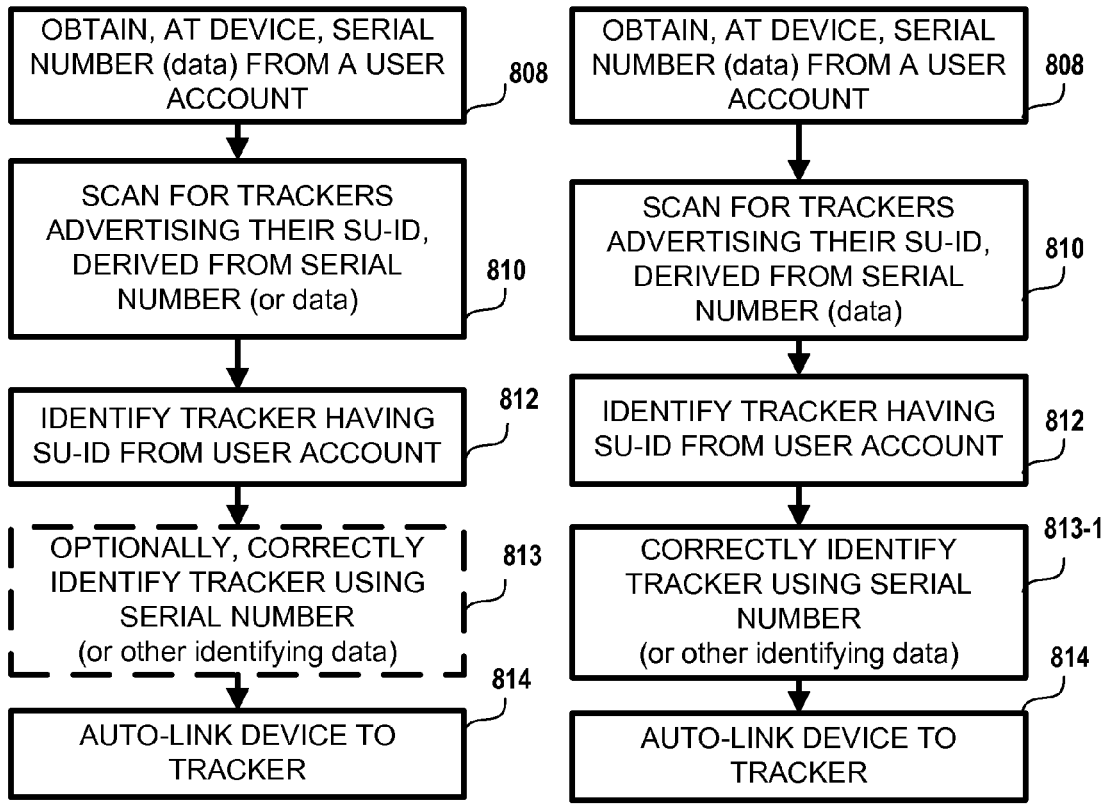
FIG. 8B  FIG. 8C

METHODS, SYSTEMS AND DEVICES FOR LINKING USER DEVICES TO ACTIVITY TRACKING DEVICES

CLAIM OF PRIORITY

This is a continuation of U.S. patent application Ser. No. 14/092,864, filed on Nov. 27, 2013, titled "Methods, Systems and Devices for Linking User Devices to Activity Tracking Devices, which is herein incorporated by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of Ser. No. 13/959,714, filed Aug. 5, 2013, titled "Methods and Systems for Identification of Event Data Having Combined Activity and Location Information of Portable Monitoring Devices", which is a continuation-in-part of U.S. patent application Ser. No. 13/759,485 (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

CROSS REFERENCE TO RELATED APPLICATION

This application is related to U.S. application Ser. No. 14/050,292, filed on Oct. 9, 2013, entitled "Methods, Systems, and Devices for Activity Tracking Device Data Synchronization with Computing Devices," which claims priority to U.S. Provisional Application No. 61/885,962, filed on Oct. 2, 2013, both of which are incorporated herein by reference.

This application is related to U.S. patent application Ser. No. 14/092,860, titled "Methods, Systems, and Devices for Automatic Linking of Activity Tracking Devices to User Devices," filed on Nov. 27, 2013, which is incorporated herein by reference.

FIELD

The present disclosure relates to systems and methods for linking communication between an activity tracking device and a client device.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness trackers are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data with complicated or confusing interfaces. In addition, updates between a tracker and a client device usually require wired connectors and/or complex syncing schemes.

It is in this context that embodiments described herein arise.

SUMMARY

Embodiments described in the present disclosure provide systems, apparatus, computer readable media, and methods for enabling activity tracking devices (ATDs) to automatically link to devices, such as user computing devices, e.g., smartphones, tablets, laptops, computing devices, etc. In one implementation, automatic linking to activity tracking devices uses logic of the ATD to enable advertising of identifier data that is picked up by a user device. The operating system executing an activity tracking application on the user device is able to link with the ATD without requiring user input or action to initiate the linking. In one example, the identifier data is a semi-unique identifier (SU-ID), that can be advertised by the ATD, so that a scanning user device can link and negotiate confirmation of a correct connection with the ATD.

In another embodiment, a method is provided. The method includes advertising, by an activity tracking device, data that includes a semi-unique identifier of the activity tracking device. The advertising of the data is configured for detection by a device that is scanning for advertised data. The method includes connecting with the device once the semi-unique identifier is found by the device and matches a copy of the semi-unique identifier obtained by the device from an activity tracking website for a user account. The method then establishing a link with the device. The linking occurring when the device verifies that the activity tracking device having the semi-unique identifier is associated to the user account. In one embodiment, the scanning, connection and link establishment occurs automatically in response to the device opening and logging into an application on the device that provides access to the user account.

In another embodiment, a tracking device configured for capture of activity for a user is provided. The tracking device includes a housing, and a sensor disposed in the housing to capture motion data associated with activity of the user. The tracking device also includes memory for storing the captured motion data and a device identification (ID) of a device that the tracking device is able to initiate connection and link therewith. The tracking device includes a processor configured to scan for a semi-unique identifier broadcasted by the device. The processor enables connection with the device with the tracking device after the semi-unique identifier is found to be of the device by the tracking device. The tracking device is configured to query or communicate with the device to obtain a device identification (ID) of the device. The processor enables the linking of the device to the tracking device when the device ID of the device matches a copy of the device ID stored in the memory of the tracking device.

Computer readable medium, storing program instructions executable by a processor, for managing auto-linking of activity tracking devices to computing devices, is also provided.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings.

FIG. 8A illustrates an example where an ATD executes operations to enable the auto-linking to occur, in one embodiment of the present invention.

FIG. 8B illustrates an example where a device can operate to establish a link with an ATD, in accordance with one embodiment of the present invention.

FIG. 8C illustrates an example where a device can operate to establish a link with an ATD and verification of the correct ATD is performed, in accordance with an embodiment of the present invention.

DETAILED DESCRIPTION

Figure 1A:
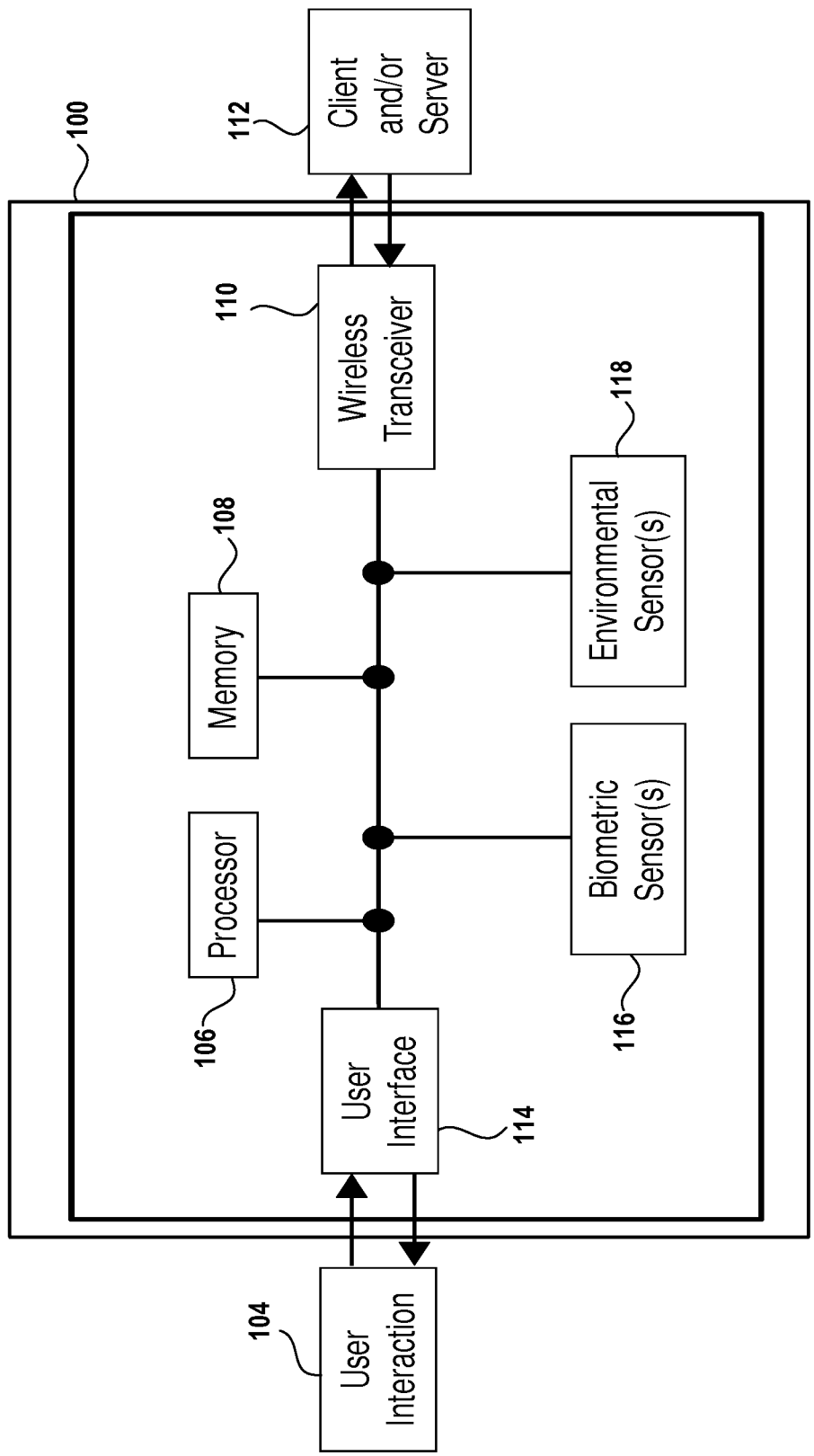
FIG. 1A shows a block diagram of an activity tracking device, in accordance with one embodiment of the present invention.

Embodiments described in the present disclosure provide systems, apparatus, computer readable media, and methods enabling activity tracking devices (ATDs) to automatically link to devices, such as user computing devices, e.g., smartphones, tablets, laptops, computing devices, etc. In the various embodiments, automatic linking to activity tracking devices are configured with logic to enable advertising of identifier data that is picked up by a user device, to enable the user device to link with the ATD without requiring user input or action to initiate the linking. In one embodiment, the identifier data is a semi-unique identifier (SU-ID), that can be advertised by the ATD, so that a user device looking to link with the ATD can find and negotiate a connection to the ATD.

In one implementation, advertising is a function carried out by logic of the ATD circuitry (e.g., firmware, hardware, software, circuits, logic, etc.), which enables a wireless data to be emitted. The emitted data can be of any size, although by making the data that is advertised small, less power is utilized by the ATD to emit the data. In one implementation, the emitted data that is advertised by the ATD is in the form of one or more bits, or one or more packets. For example, packets may be referred to as advertising packets. For purpose of further example, such advertising packets may be in the form or format defined by a Bluetooth Low Energy (BT LE) standard. In other embodiments, data or packets can be defined by any protocol, standard, or non-standard format.

In the example of the BT LE standard, the ATD acts as a slave device that is able to announce that it has something to transmit to other devices that are "scanning" "Advertising" messages can also include an event or a measurement value, or some form of identifier data. In one embodiment, the logic of the ATD is configured to advertise part of or derived from the device identifier (e.g., the device identifier being a serial number), which is referred to herein as a semi-unique identifier (SU-ID). Although various sizes or parts or all of the device serial number can be advertised, advertising less than the whole saves power consumption by the ATD, which extends use between charging. For one implementation, the SU-ID is 16 bits. In one example, the 16 bits are fairly evenly distributed, so that many devices are eliminated by the scanning, thus reducing attempted connections with ATDs that do not advertise the SU-ID. Although an SU-ID is not completely unique, it is unique enough that a user's device should only have to connect to a very small number of possible matches.

As noted above, SU-IDs may be evenly or at least partially distributed to avoid having too many trackers advertise the same SU-ID. In one implementation, the SU-ID is derived, generated, or obtained from the serial number of the ATD (e.g., the SU-ID may be part of the serial number). In one configuration of the serial number, one of the fields in the serial number is data that represents "seconds from midnight" on the day of manufacture. Thus, the SU-ID can be a bit(s) value that represents the "seconds from midnight." In one example, when the manufacturing line is running throughout the day (or over a period of time) and at a relatively consistent rate (or some changing interval or rate) it can be assumed that the SU-ID has an even chance to be on any one of those seconds.

By selecting a value for the SU-ID that is changing for different ATDs, the SU-ID can be viewed to be substantially evenly distributed. As a result, there is a smaller chance of multiple trackers in the same vicinity having the same SU-ID. Thus, the SU-ID is not unique across all trackers like the serial number. For example only, if the SU-ID ranged from 1-1000, it could be expected that there is a 1 in 1000 chance for two trackers to have the same SU-ID. However, if the distribution was skewed so that 50% had an SU-ID between 1-100, then given two trackers it is much more likely that they would have the same SU-ID. When seconds after midnight is used as the semi-unique identifier, there will be 3,600 different possible seconds that can be assigned to serial numbers. Broadly speaking, the SU-ID is selected/assigned to be a number that changes over time, so there is a reduced likelihood that two proximate trackers will have the same SU-ID.

In an alternate embodiment, the SU-ID can be generated by the ATD, by a device such as a phone, tablet, portable device, laptop or any computing device, or can be generated by the website 350. In some embodiments, the SU-ID is randomly generated. If the SU-ID is randomly generated, the SU-ID need not be part of the serial number and need not be generated based on the serial number. Accordingly, it should be understood that the generation of the SU-ID can take on various configurations. If randomly generated, the SU-ID can be represented by data, such as one or more bits. The data can also be, in one embodiment alphanumeric data, or digitally represented data. In one implementation, the random SU-ID can be produced by a random number generator, which produces random code or data.

In one embodiment, an application (APP) is installed on the user's device. For example, the user's device may operate any number of operating systems, such as Apple Inc.'s iOS, Google Inc.'s Android, Microsoft Inc.'s Windows, Blackberry Inc.'s OS, etc. As noted above, the device can have any form factor, such as a smartphone, a tablet, a laptop, a personal digital assistant, glasses, a computer, etc. In one embodiment, the APP installed on the device will be an activity tracking application (e.g., see FIG. 3, item 202). For purposes of example, Apple's iOS is described, but as noted above, this process can be made to operate using any operating system on any type of device, so long as wireless communication is enabled. Therefore, the activity tracking application 202 will communicate with the operating system of the device, e.g., iOS, which will detect that the APP 202 has been launched.

The APP 202 knows the SU-ID of devices registered to the user account. In one example, the site will send the serial number to the user device, which includes the SU-ID, or the site can send the user device the SU-ID itself. The iOS can then use the SU-ID to identify the ATDs that are advertising the SU-IDs that match, and the iOS can connect to each one of the ATDs to determine which ATD is associated with the user account. In most implementations, few ATDs will be present in the vicinity of the user's device, so it is likely that the iOS will only connect to an ATD that is advertising the matching SU-ID. Once the correct ATD is found, the iOS will automatically link to the ATD.

In one embodiment, what is meant by automatic is that the user need not initiate the linking process. Once the user opens the APP on the user's device, the linking process of searching for the ATD that is advertising the SU-ID and the eventual linking operates without user intervention (e.g., does not require the user to click on icons, controls, configuration interfaces, etc. on the APP to initiate the linking process with an ATD).

In an alternate embodiment, a unique ID (UID) of the ATD can be advertised. Although this will consume more power than a SU-ID, some embodiments may require more accurate identification of the ATD, such as when speed is needed to acquire a link to an ATD (e.g., avoids connection to multiple matches, even if the matches are small).

The computing device can be a computer that executes an activity tracking application (APP). The computing device can take on any form, so long as it can process information, load and execute an application, and can communicate wirelessly with the activity tracking device. For example purposes, the computing device can be a computer, a tablet computer, a smart phone, a tablet, a laptop, a desktop, a watch computer, glasses computer, or any device having access to memory and processing power.

In one embodiment, the ATD is configured collect motion data, activity data, and other data, such as altitude or relative altitude data, barometric pressure data, heart rate data, temperature data, alarm data, goal data, history status data, processed data, raw data, etc.

Additionally, although the computing device may usually have access to an Internet connection, every transfer between the activity tracking device and the computing device does not require Internet connection. When the computing device is connected to the Internet, the computing device can then sync data to a server. The server, in one embodiment, can be one or more distributed servers, data centers, virtualized servers in distributed data centers, etc. The server, in one embodiment, executes an activity management application that enables user account access to metrics associated with activity tracking devices.

It should be noted that there are many inventions described and illustrated herein. The inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

FIG. 1A shows a block diagram of an activity tracking device 100, in accordance with one embodiment of the present invention. The activity tracking device 100 is contained in a housing, which may be worn or held by a user. The housing may be in the form of a wristband, a clip on device, a wearable device, or may be held by the user either in the user's hand or in a pocket or attached to the user's body. The activity tracking device 100 includes device components 102, which may be in the form of logic, firmware, storage, and glue logic, one or more processors, microelectronics, and interfacing circuitry. In one example, the components 102 will include a processor 106, memory 108, a wireless transceiver 110, a user interface 114, biometric sensors 116, and environmental sensors 118.

The environmental sensors 118 may be in the form of motion detecting sensors. In some embodiments, a motion sensor can be one or more of an accelerometer, or a gyroscope, or a rotary encoder, or a calorie measurement sensor, or a heat measurement sensor, or a moisture measurement sensor, or a displacement sensor, or an ultrasonic sensor, or a pedometer, or an altimeter, or a linear motion sensor, or an angular motion sensor, or a multi-axis motion sensor, or a combination thereof. The biometric sensors 116 can be defined to measure physiological characteristics of the user that is using the activity tracking device 100. The user interface 114 provides a way for communicating with the activity tracking device 100, in response to user interaction 104. The user interaction 104 can be in the form of physical contact (e.g., without limitation, pressing a button, tapping, sliding, rubbing, multiple taps, gestures, etc.).

In some embodiments, the user interface 114 is configured to receive user interaction 104 that is in the form of noncontact input. The noncontact input can be by way of proximity sensors, button presses, touch sensitive screen inputs, graphical user interface inputs, voice inputs, sound inputs, etc. The activity tracking device 100 can communicate with a client and/or server 112 using the wireless transceiver 110. The wireless transceiver 110 will allow the activity tracking device 100 to communicate using a wireless connection, which is enabled by wireless communication logic. The wireless communication logic can be in the form of a circuit having radio communication capabilities. The radio communication capabilities can be in the form of a Wi-Fi connection, a Bluetooth connection, a low-energy Bluetooth connection, or any other form of wireless tethering or near field communication. In still other embodiments, the activity tracking device 100 can communicate with other computing devices using a wired connection (not shown). As mentioned, the environmental sensors 118 can detect motion of the activity tracking device 100.

The motion can be activity of the user, such as walking, running, stair climbing, etc. The motion can also be in the form of physical contact received on any surface of the activity tracking device 110, so long as the environmental sensors 118 can detect such motion from the physical contact. As will be explained in more detail below, the physical contact may be in the form of a tap or multiple taps by a finger upon the housing of the activity tracking device 100.

Figure 1B:
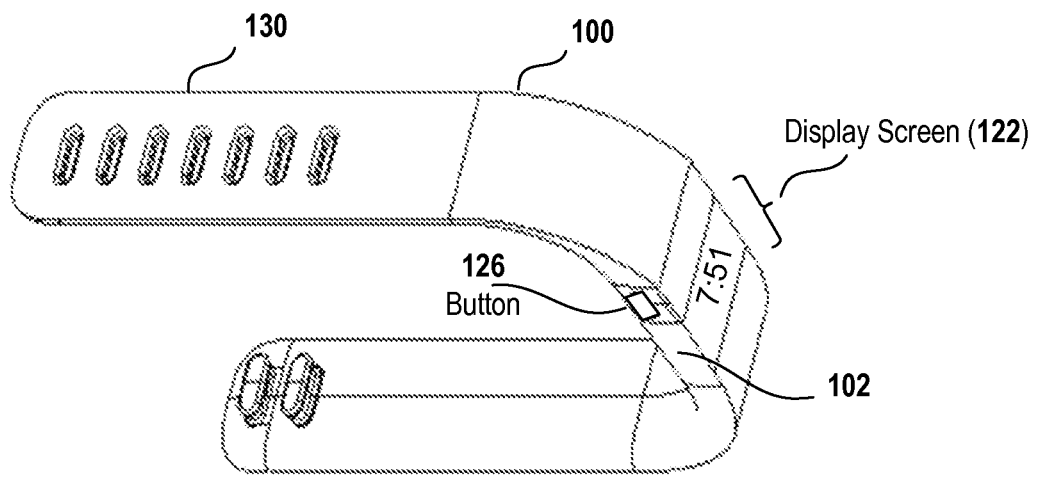
FIG. 1B illustrates an example of an activity tracking device, in accordance with one embodiment of the present invention.

FIG. 1B illustrates an example of an activity tracking device 100 having a housing 130 in the form of a wearable wrist attachable device. The sensors of the activity tracking device 100 can, as mentioned above, detect motion such as physical contact that is applied and received on a surface of the housing 130. In the example shown, the physical contact is in the form of a tap or multiple taps on the surface. Device components 102 are, in one embodiment, contained within the housing 130. The device components can include circuits, firmware (e.g., updatable firmware), processors, batteries, logic, etc. The location at which the device components 102 are integrated into the housing 130 can vary. For example, the device components 102 can be integrated throughout various locations around the housing 130, and not limited to the central portion of the wrist attachable device or chip device. In some embodiments, the device components 102 can be integrated into or with a smart watch device.

In other embodiments, the device components 102 are positioned substantially in a central position of the wrist attachable device, such as under or proximate to a location where a display screen 122 is located. In the illustrated example, the housing 130 also includes a button 126. The button 126 can be pressed to activate the display screen 122, navigate to various metrics displayed on the screen 122, or turn off the screen 122.

Figure 1C:
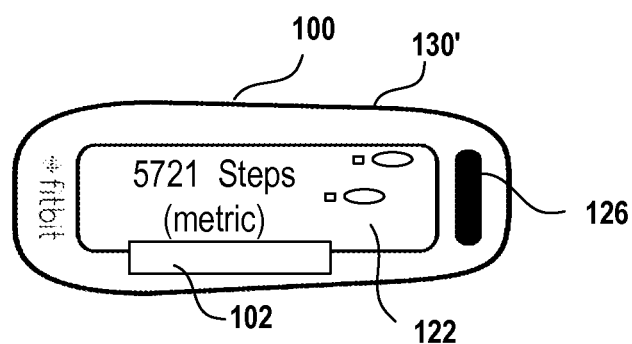
FIG. 1C illustrates another example of an activity tracking device, in accordance with one embodiment of the present invention.

FIG. 1C illustrates another example of an activity tracking device 100, in accordance with one embodiment of the present invention. The form factor of the activity tracking device 100 is shown as a clickable device that includes a screen 122, a button 126, and device components 102 integrated within the housing 130. The housing 130 can include a clip that allows for attachment to clothing or articles of the user, or to simply place the device within a pocket or holder of the user. Accordingly, the physical contact shown with respect to FIG. 1B can also be implemented upon the surface of activity tracking device 100 of FIG. 1C. It should be understood, therefore, that the form factor of the activity tracking device 100 can take on various configurations and should not be limited to the example configurations provided herein.

Figure 2:
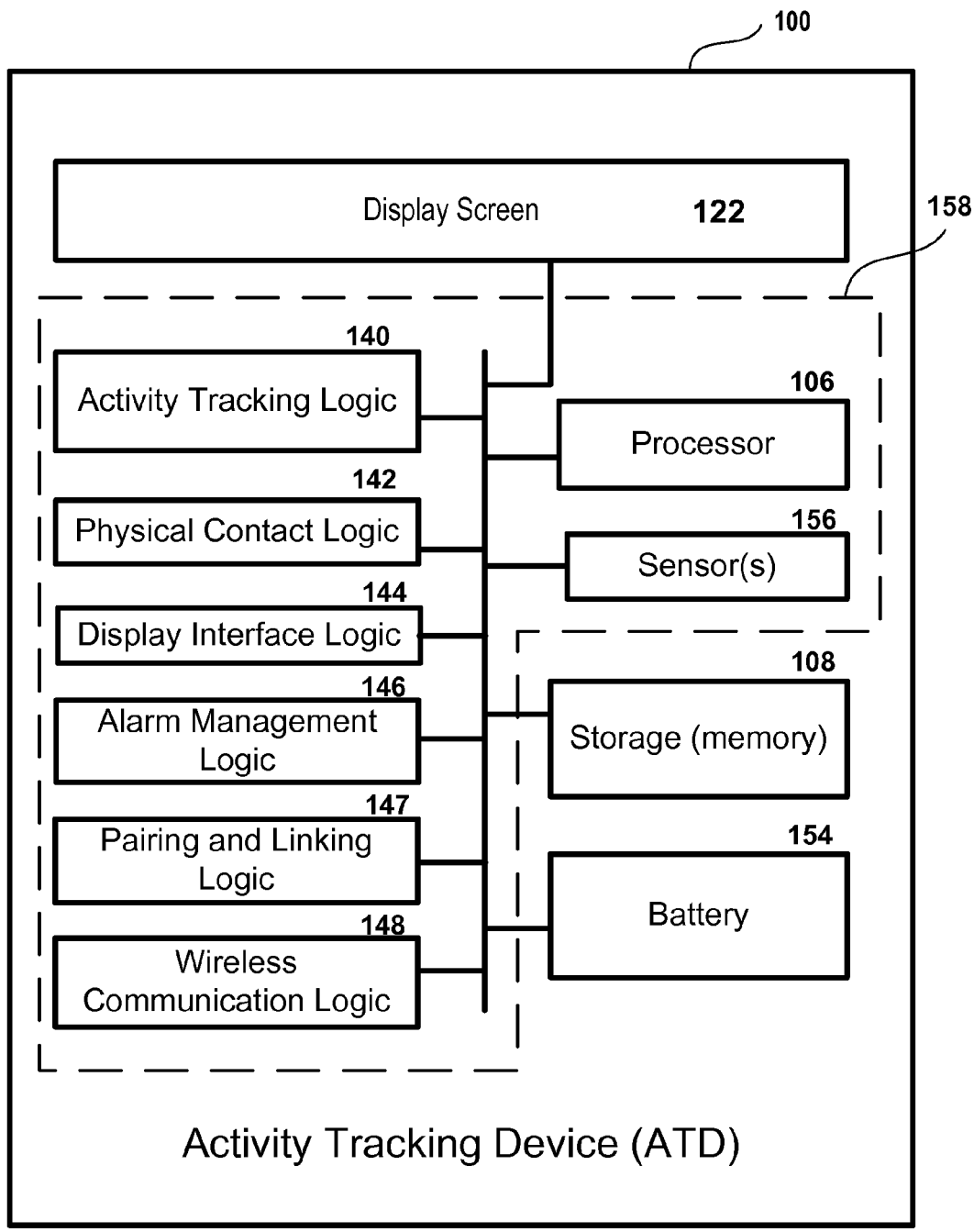
FIG. 2 illustrates an example of activity tracking device including example components utilized for tracking activity and motion of the device, and associated interfaces to a display screen, in accordance with one embodiment of the present invention.

FIG. 2 illustrates an example of activity tracking device 100 of FIGS. 1A-1C, showing some additional example components utilized for tracking activity and motion of the device, and associated interfaces to display screen 122. In one example, a finger of a user can be used to tap and provide physical contact onto any surface of activity tracking device 100. The physical contact, when sensed by sensors 156 of the activity tracking device 100, will cause a response by the activity tracking device 100, and therefore provide some metric on the display screen 122. In one embodiment, examples of a display screen 122 can include, but are not limited to, liquid crystal display (LCD) screens, light emitting diode (LED) screens, organic light emitting diode (OLED) screens, plasma display screens, etc.

As shown in FIG. 2, the activity tracking device 100 includes logic 158. Logic 158 may include activity tracking logic 140, physical contact logic 142, display interface logic 144, alarm management logic 146, pairing and linking logic 147, wireless communication logic 148, processor 106, and sensors 156. Other logic can be provided in the form of firmware, which can be updated from time to time. In one example, the firmware, software, logic, etc. can execute and manage the pairing and linking logic 147. Additionally, storage (e.g. memory) 108, and a battery 154 can be integrated within the activity tracking device 100. The activity tracking logic 140 can include logic that is configured to process motion data produced by sensors 156, so as to quantify the motion and produce identifiable metrics associated with the motion.

Some motions will produce and quantify various types of metrics, such as step count, stairs climbed, distance traveled, very active minutes, calories burned, etc. The physical contact logic 142 can include logic that calculates or determines when particular physical contact can qualify as an input. To qualify as an input, the physical contact detected by sensors 156 should have a particular pattern that is identifiable as input. For example, the input may be predefined to be a double tap input, and the physical contact logic 142 can analyze the motion to determine if a double tap indeed occurred in response to analyzing the sensor data produced by sensors 156.

In other embodiments, the physical contact logic can be programmed to determine when particular physical contacts occurred, the time in between the physical contacts, and whether the one or more physical contacts will qualify within predefined motion profiles that would indicate that an input is desired. If physical contact occurs that is not within some predefined profile or pattern, the physical contact logic will not indicate or qualify that physical contact as an input.

The display interface logic 144 is configured to interface with the processor and the physical contact logic to determine when specific metric data will be displayed on the display screen 122 of the activity tracking device 100. The display interface logic 144 can act to turn on the screen, display metric information, display characters or alphanumeric information, display graphical user interface graphics, or combinations thereof. Alarm management logic 146 can function to provide a user interface and settings for managing and receiving input from a user to set an alarm. The alarm management logic can interface with a timekeeping module (e.g., clock, calendar, time zone, etc.), and can trigger the activation of an alarm. The alarm can be in the form of an audible alarm or a non-audible alarm.

A non-audible alarm can provide such alarm by way of a vibration. The vibration can be produced by a motor integrated in the activity tracking device 100. The vibration can be defined to include various vibration patterns, intensities, and custom set patterns. The vibration produced by the motor or motors of the activity tracking device 100 can be managed by the alarm management logic 146 in conjunction with processing by the processor 106. The wireless communication logic 148 is configured for communication of the activity tracking device with another computing device by way of a wireless signal. The wireless signal can be in the form of a radio signal. As noted above, the radio signal can be in the form of a Wi-Fi signal, a Bluetooth signal, a low energy Bluetooth (e.g., LE Bluetooth) signal, or combinations thereof. The wireless communication logic can interface with the processor 106, storage 108 and battery 154 of device 100, for transferring activity data, which may be in the form of motion data or processed motion data, stored in the storage 108 to the computing device.

In one embodiment, processor 106 functions in conjunction with the various logic components 140, 142, 144, 146, 147, and 148. The processor 106 can, in one embodiment, provide the functionality of any one or all of the logic components. In other embodiments, multiple chips can be used to separate the processing performed by any one of the logic components and the processor 106. Sensors 156 can communicate via a bus with the processor 106 and/or the logic components. The storage 108 is also in communication with the bus for providing storage of the motion data processed or tracked by the activity tracking device 100. Battery 154 is provided for providing power to the activity tracking device 100.

Figure 3:
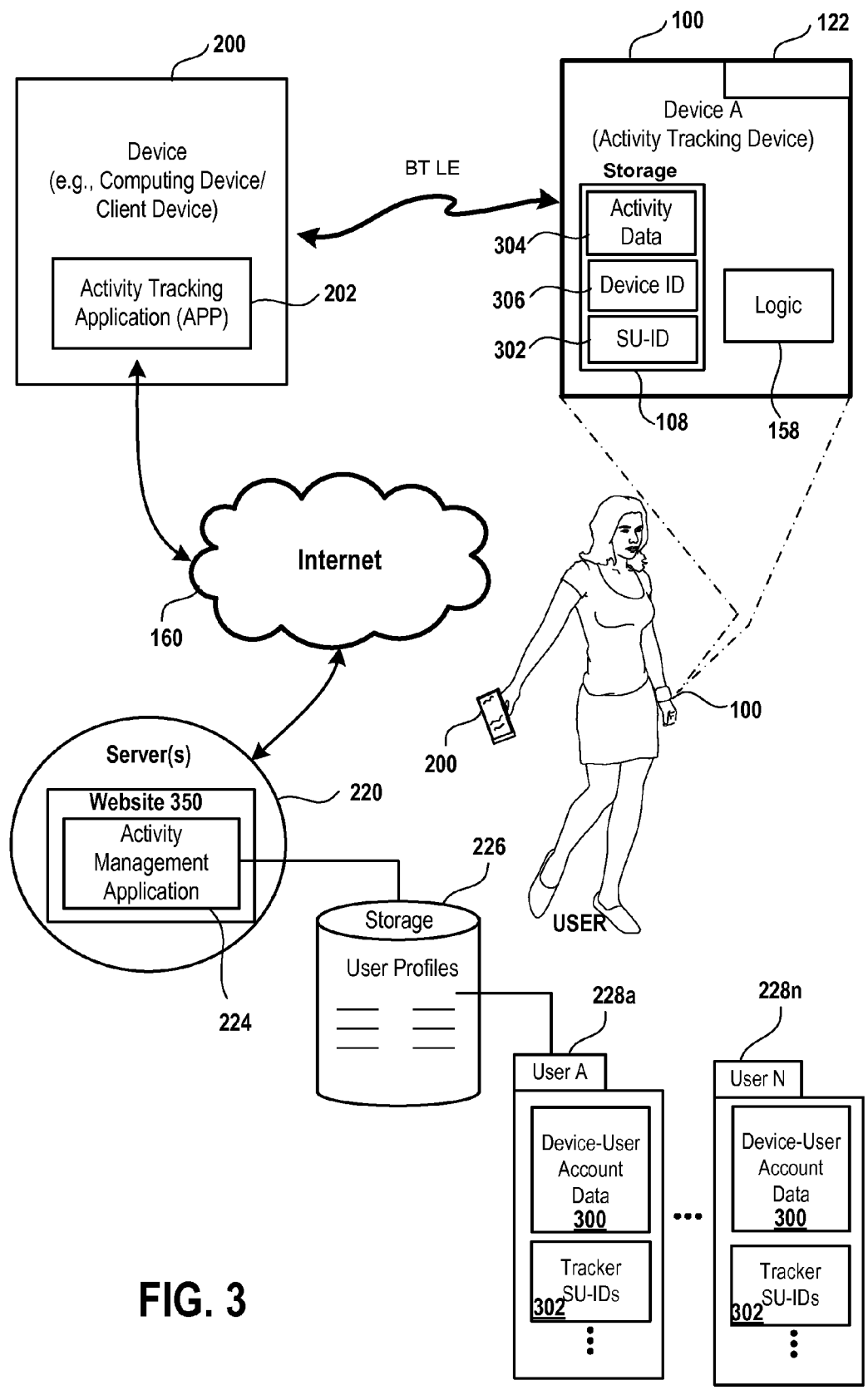
FIG. 3 illustrates an example of activity tracking device in communication with a device and interfaces with a server, in accordance with one embodiment of the present invention.

FIG. 3 illustrates an example of activity tracking device 100 in communication with a device 200. Device 200 is a computing device that is capable of communicating wirelessly with activity tracking device 100 and with the Internet 160. Device 200 can support installation and execution of applications (e.g., APPs, mobile APPs, etc.). Such applications can include an activity tracking application 202. Activity tracking application 202 can be downloaded from a server or locally installed. The server can be a specialized server or a general server that provides applications to devices, such as an application store. Once the activity tracking application 202 is installed in the device 200, the device 200 can communicate or be set to communicate with activity tracking device (ATD) 100 (Device A). As described below, the ATD 100 is first paired to a website that manages the ATD and provide user access (e.g., via a user account) to metrics and information produced by the ATD. The pairing to the site can be by way of the user device (e.g., using the OS of a smartphone or a dongle device), having access to the Internet and the website that manages the ATD.

The device 200 can be a smartphone, a handheld computer, a tablet computer, a laptop computer, a desktop computer, or any other computing device capable of wirelessly interfacing with Device A. In one embodiment, the device can also have circuitry and logic for communicating with the Internet. However, it should be understood that an Internet connection is not required to enable the device 200 to communicate with the activity tracking device 100.

In one embodiment, device 200 communicates with activity tracking device 100 over a Bluetooth connection. In one embodiment, the Bluetooth connection is a low energy Bluetooth connection (e.g., Bluetooth LE, BLE, or Bluetooth Smart). Low energy Bluetooth is configured for providing low power consumption relative to standard Bluetooth circuitry. Low energy Bluetooth uses, in one embodiment, a 2.4 GHz radio frequency, which allows for dual mode devices to share a single radio antenna. In one embodiment, low energy Bluetooth connections can function at distances up to 50 meters, with over the air data rates ranging between 1-3 megabits (Mb) per second. In one embodiment, a proximity distance for communication can be defined by the particular wireless link, and is not tied to any specific standard. It should be understood that the proximity distance limitation will change in accordance with changes to existing standards and in view of future standards and/or circuitry and capabilities.

Device 200 can also communicate with the Internet 160 (e.g., cloud) using an Internet connection. The Internet connection of the device 200 can include cellular connections, wireless connections such as Wi-Fi, and combinations thereof (such as connections to switches between different types of connection links). The device, as mentioned above, can be a smartphone or tablet computer, or any other type of computing device having access to the Internet and with capabilities for communicating with the activity tracking device 100.

In one embodiment, a server 220 is also provided, which is interfaced with the Internet 160. The server 220 (or servers) can include a number of applications that service the activity tracking device 100, and the associated users of the activity tracking device 100 by way of user accounts. For example, the server 220 can include an activity management application 224. The activity management application 224 can include logic for providing access to various devices 100, which are associated with user accounts managed by server 220. The activity management application 224 can be presented by a website 350. The website 350 can provide user interfaces that enable access to user accounts, user data, identification of tracking devices paired with the site (e.g., website), historical data, information, social data, social connections, rewards, earned badges, etc. Server 220 can include storage 226 (or multiple storage repositories, which can include local storage, distributed storage, data center storage, etc.) that includes various user accounts and associated user profiles. The user account 228a for user A and the user account 228n for user N are shown to include various information.

The information can include, without limitation, device-user account data 300, system configurations, user configurations, settings and data, etc. The storage 226 will include any number of user profiles, depending on the number of registered users having user accounts for their respective activity tracking devices. It should also be noted that a single user account can have various or multiple devices associated therewith, and the multiple devices can be individually customized, managed and accessed by a user.

Data from multiple ATDs can also be collected and associated to a user account of the site. In one configuration, logic of the site can manage data from more than one device per user account. The data can be pre-assigned or organized for each tracking device or can be blended or combined based on rules of priority. In other embodiments, metrics collected from multiple devices can processed to provide refined metrics. The refined metrics can then be accessed, presented or viewed on the site 350 or on a device accessing the user account.

In one embodiment, the user account will include the semi-unique identifier (SU-ID) of each device associated with the user account. As described herein, the SU-ID, in one embodiment, is part of the serial number of the ATD (e.g., a 16 bit portion of the serial number). In one embodiment, the user account managed by the website 350 can also store the complete serial number in association with the user accounts 228. As noted above, the initial pairing of the tracker to the site may include having the tracker send the complete serial number to the site. Thus, the site will have the serial number, which will include the SU-ID.

It should be understood that the SU-ID can be defined to include less or more of the complete serial number, and therefore the 16 bit example is just that, an example.

During an initial paring (or re-pairing) of the ATD to the site, the SU-ID of the ATD is provided to the site. As noted above, the ATD, in one example will send the complete serial number to the site, which will include the SU-ID. The site, in storage 302, will then store the serial number, which includes the SU-ID of the tracker in association with the user account. Then, the ATD uses the SU-ID in its advertising to enable automatic linking, as described herein.

As further shown, the ATD 100, in one embodiment, will include storage 108 that can store activity data 304, device ID 306, and the SU-ID 302. As noted above, the device ID 306 may be the serial number of the ATD 100. The SU-ID 302 is a portion of the serial number. In one example, only the device ID 306 is stored, and to implement the advertising, the ATD accesses the SU-ID part of the serial number. This information is stored in the ATD 100. The logic 158 of the ATD, in one embodiment, will include firmware, logic, software, that enables the generation or access of the SU-ID 302, using the device ID 306 (i.e., the serial number).

The activity data of the ATD can be processed to identify a plurality of metrics associated with the motion data or other information. The metrics can be shown in various graphical user interfaces of a website enabled by the server 220. The website can include various pages with graphical user interfaces for rendering and displaying the various metrics for view by the user associated with the user account. In one embodiment, the website can also include interfaces that allow for data entry and configuration by the user.

The configurations may include defining which metrics will be displayed on the activity tracking device 100. In addition, the configurations can include identification of which metrics will be a first metric to be displayed on the activity tracking device. The first metric to be displayed by the activity tracking device can be in response to a user input at the activity tracking device 100. As noted above, the user input can be by way of physical contact. The physical contact is qualified by the processor and/or logic of the activity tracking device 100 to determine if the physical contact should be treated as an input. The input can trigger or cause the display screen of the activity tracking device 100 to be turned on to display a specific metric, that is selected by the user as the first metric to display. In another embodiment, the first metric displayed in response to the input can be predefined by the system as a default.

The configuration provided by the user by way of the server 220 and the activity management application 224 can also be provided by way of the activity tracking application 202 of the computing device 200. For example, the activity tracking application 202 can include a plurality of screens that also display metrics associated with the captured motion data of the activity tracking device 100. The activity tracking application 202 can also allow for user input and configuration at various graphical user interface screens to set and define which input will produce display. The configuration can also allow a user to select a different tracker to pair with at various times, such as when a user account is associated with more than one tracker device.

Figure 4:
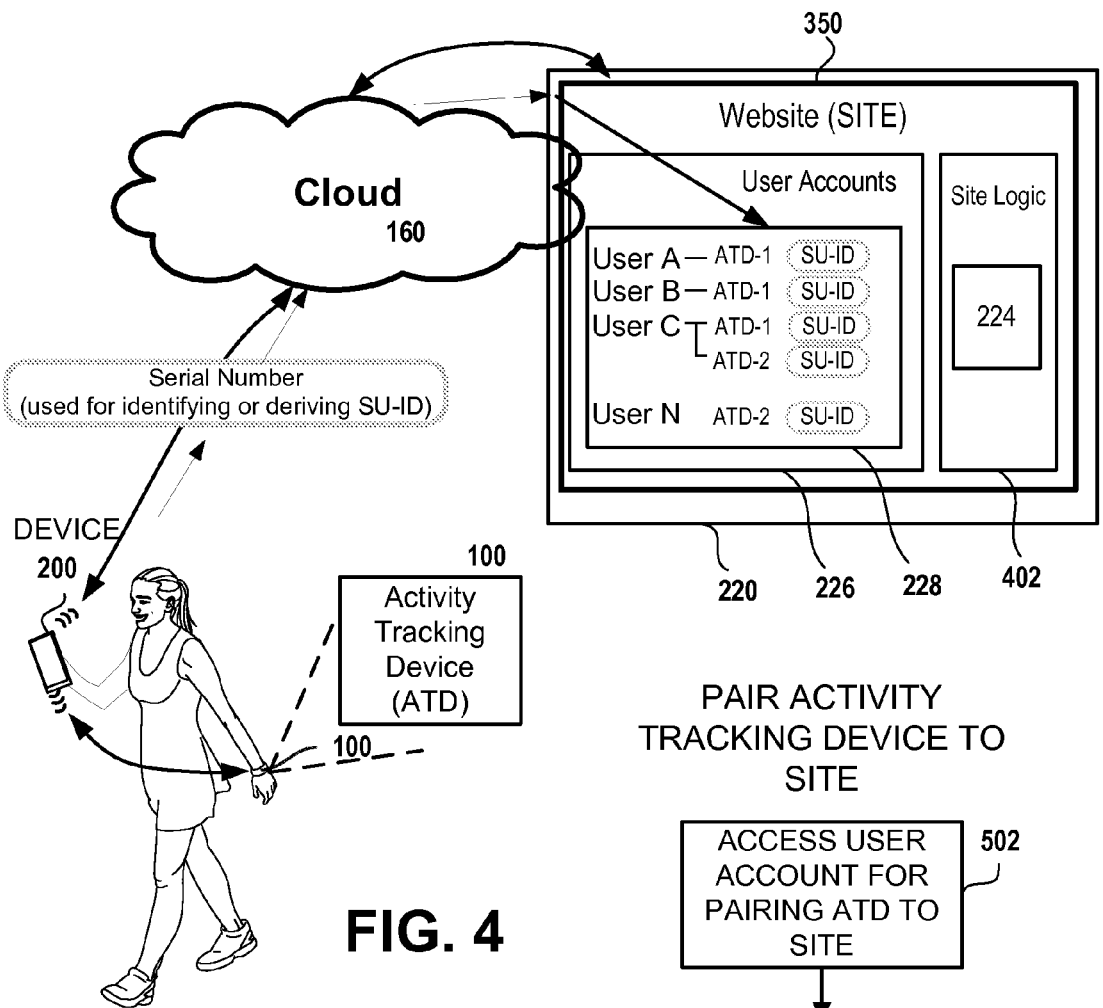
FIG. 4 illustrates an embodiment where a user is wearing an activity tracking device (ATD) 100, and is using a device, in accordance with one embodiment of the present invention.

FIG. 4 illustrates an embodiment where a user is wearing an activity tracking device (ATD) 100, and is using a device 200, in accordance with one embodiment of the present invention. In this implementation, the user is in the process of pairing ATD 100 to the website 350 (site). The ATD 100 includes firmware with process instructions for generating the SU-ID. The ATD also is configured to communicate the serial number of the ATD to the device 200. The device 200 will then send the serial number to the website 350 via the Internet 160. In another embodiment, the user can pair the ATD 100 to the site using a dongle connected to a computer that has an Internet connection. In this embodiment, the dongle can communicate wirelessly to the ATD, and the user can login to the website 352 allow for the pairing operation of the ATD to the user's account.

As shown, the website 350 may include a plurality of user accounts 228, and each user account will be associated to trackers (ATDs) that have been paired to the user's account. In this example, the user is user A, and user a has ATD-1 paired to her account. In addition, the account of user A will be associated with the SU-ID of the ATD-1. Association to the SU-ID can be by way of the complete serial number, obtained from the ATDs, each which includes the SU-IDs. In a similar manner, other users, such as users B, C, N, can associate one or more trackers to their respective user accounts. In the case of user C, two trackers (ATD-1 and ATD-2) have been associated to user C's account, along with an association, relation or pointers/references to the respective SU-IDs (e.g., and in one example, the respective serial numbers).

In one embodiment, the ATD 100 is configured to transfer its serial number to the website 350 for association to the user's account, and the respective ATD. The website 350, as shown, may be managed by servers 220, which are in communication with its storage 226. The user accounts 228 are defined in storage which is accessible to the server 220. Site logic 402 can include an activity management application 224. The activity management application 224 can function to manage the user accounts 228. The management of the assigned ATDs and respective SU-IDs can also be managed by the site logic 402.

Figure 5:
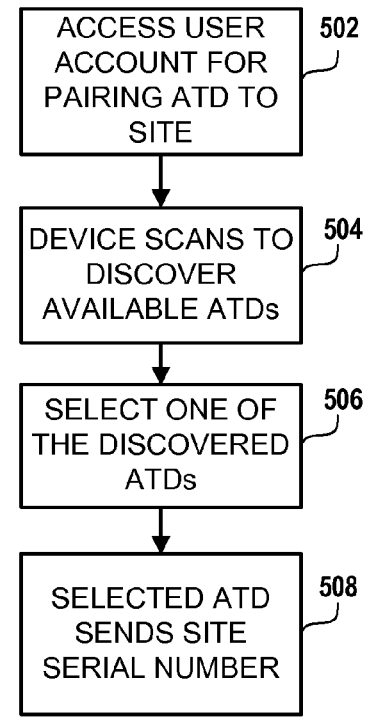
FIG. 5 illustrates an embodiment where in ATD is paired to a site, in accordance with one embodiment of the present invention.

FIG. 5 illustrates an embodiment where in ATD is paired to the site 350, in accordance with one embodiment of the present invention. In operation 502, the user account is accessed for pairing an ATD to the site. The user account can be, for example a new user, or an existing user. In each case, users can add ATDs (e.g., one or more) to their account, and the associated SU-IDs. In operation 504, the device 200 can scan to discover an available ATD that the user may be wishing to pair to the user account at the site. The device performing the scanning can also be a dongle, in another embodiment. In operation 506, one of the discovered ATDs is selected by the user for association to the user account.

Firmware (or logic) operating on the ATD 100 can communicate with the device during the pairing operation. During this pairing operation, the ATD 100 can send the serial number of the ATD 100 to the device 200 or dongle. The device 200 or dongle will then send the serial number (e.g., including the SU-ID for the ATD 100) to the site 350, which is then associated to the user's account as shown in FIG. 4.

Figure 6:
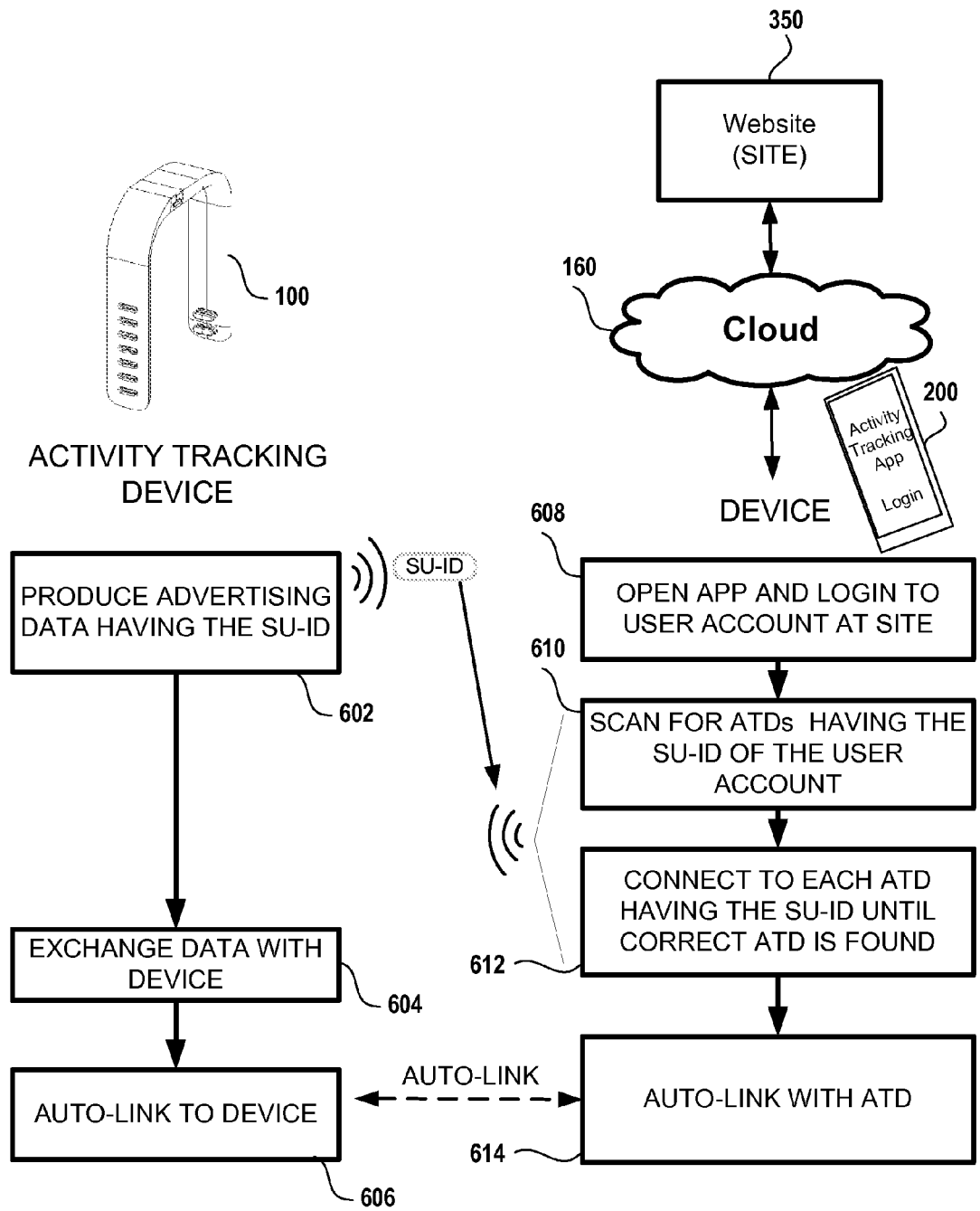
FIG. 6 illustrates one embodiment where in ATD is in communication with a device to enable linking of the ATD with the device, during operation.

FIG. 6 illustrates one embodiment where in ATD 100 is in communication with a device 200 to enable linking of the ATD 100 with the device 200, during operation. For instance, once the ATD 100 has been associated to the user's account on the site and the SU-ID is known to the site, later communication of the ATD 100 to the device 200 will require establishing a link. In this example, the ATD 100 will produce an advertisement message that includes the SU-ID of the ATD 100 in operation 602.

On the device side, the device 200 will have an activity tracking application, which the user can log into to access the user account at the site (e.g., website 350). The activity tracking application on the device 200 will make connection to the user account at the site, and will be provided with the serial numbers (which include the SU-ID) for one or more ATDs associated with the account.

In operation 608, the app on the device 200 is opened and logged into to access the user account at the site. In operation 610, the device 200 will scan for ATDs having the SU-ID of the user account. The app executing on the device 200 will also utilize functionality of the operating system to enable the scanning for ATDs, and the advertised messages coming from ATDs. In operation 612, the device 200, utilizing the operating system (in the example of Apple Inc., iOS) and logic of the app will enable connection to each of the ATDs having SU-ID, which are found. Normally, only one device will be found in proximity to the device 200, provided no other users with an ATD are in the vicinity.

In one implementation, even if one only one device is found with the correct SU-ID, the process will still verify that the correct ATD has been found. This process, in one example, uses all or part of the full serial number to confirm that the ATD found is the correct ATD for the user that logged into the app on device 200 or some other device. As noted above, the site 350 may provide the full serial number to the device 200, so the device 200 will have access to the full serial number to make the confirmation or verification that the SU-ID found is for the correct ATD that belongs to the user logged into the app via the device 200.

In other embodiments where more than one user is wearing an ATD in a particular vicinity, it is likely that more than one ATD will have the same SU-ID. However, the number will be small relative to not searching for or filtering for the SU-ID known to the app executed by device 200.

Because the set of possible ATDs generating advertisement messages with the same SU-ID is substantially reduced, device 200 will only have to connect to that small subset of ATDs to determine if the correct ATD for the user is found.

If multiple ATDs have the same SU-ID, the app can connect to each one in turn and check against the complete serial number or parts of the serial number or other identifying data. Without the SU-ID, the app would have to connect with many more ATDs to search for the desired ATD.

In operation 604, ATD 100 will exchange data with device 200, during the period when operations 610 and 612 are executed by device 200. In operation 614, device 200 has identified the correct ATD 100 to link with, and an auto-link operation is performed with ATD 100, in operation 606. As used herein, auto-linking means that device 200 did not require the user to select to pair to a specific ATD 100 when logging into the app on device 200. Instead, the user simply logs into the app 200, and the logic in the app and the OS (operating system) on device 200 scan for and identify the correct ATD 100, and established the link automatically. This automatic linking occurs without user input, aside from having the user open and login to the app on device 200.

Figure 7A:
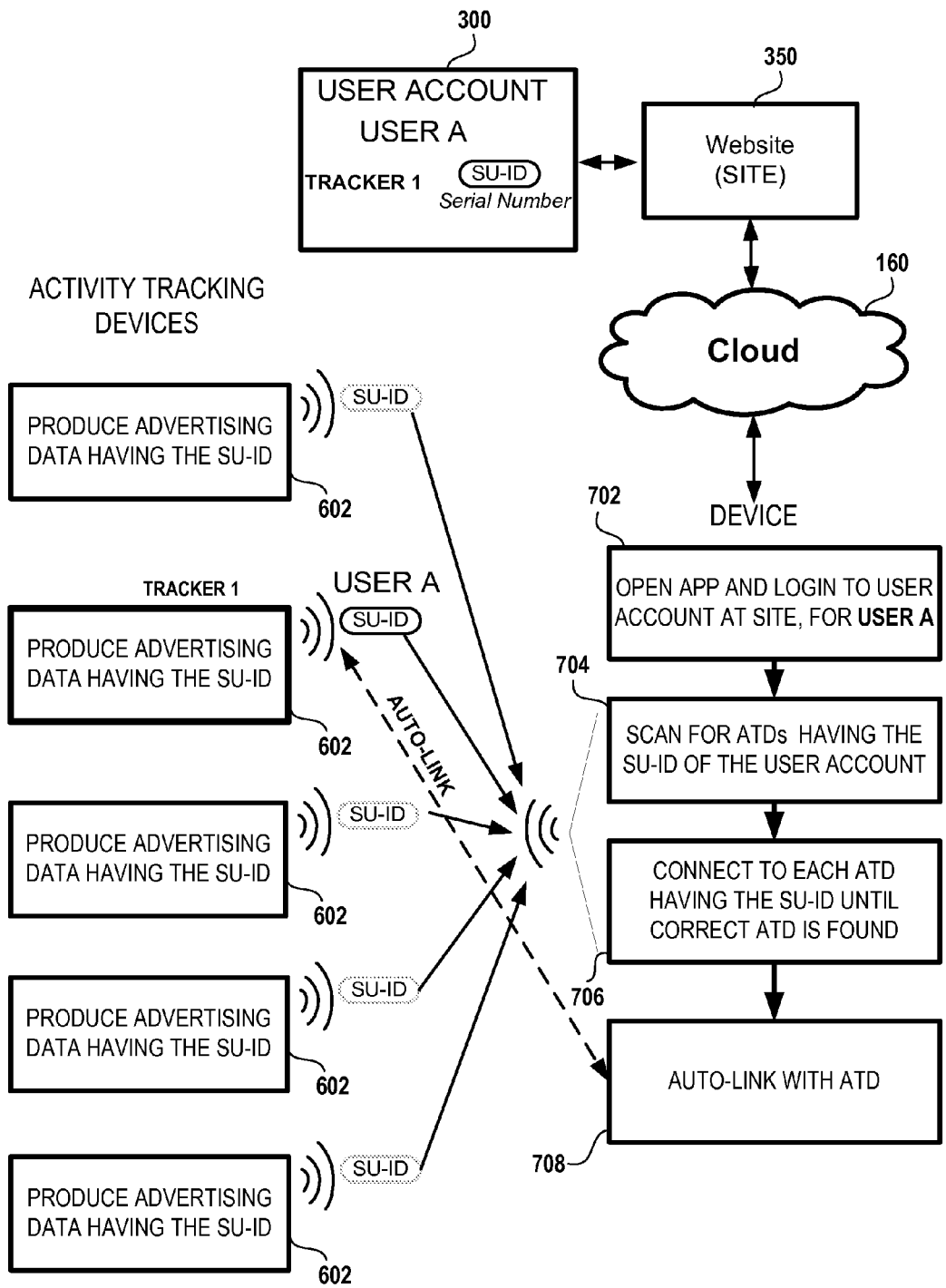
FIG. 7A illustrates one example where multiple ATDs may be present in a particular location where the user device is attempting to connect to the correct ATD of a specific user, in accordance with one embodiment of the present invention.

FIG. 7A illustrates one example where multiple ATDs may be present in a particular location where the user device is attempting to connect to the correct ATD of a specific user, in accordance with one embodiment of the present invention. The user account 300 is shown to be the user account of user A, and the user account has associated therewith (e.g., previously paired to) tracker 1, and SU-ID. The user account 300 may be stored in storage accessible by website 350, over the cloud Internet 160. The device, which may be device 200, will have access to the website 350 and the user account. As in the embodiment of FIG. 6, the device 200 will include an app, such as an application tracking application. The app can then be opened and logged into to initiate the auto linking. The auto linking will take place without having the user select any linking operation, and therefore operates in the background.

In operation 702, the app is opened and logged into for user A, at the site. For example, the app will establish Internet connection to the website 350 to enable access to user A's account. During this time, activity tracking devices in the vicinity may be generating 602 advertisement messages with their respective SU-IDs. In operation 704, the device 200 can scan for ATDs having the SU-ID of the user account. As noted above, the device can utilize the scanning operation provided by the operating system, to identify or locate advertisement data provided by ATDs in the vicinity.

In one embodiment, the vicinity in which advertisement messages can be detected can be up to about 50 meters, or within local environmental constraints or restrictions or capabilities of a Bluetooth LE communication signal. In other embodiments, further distances can be defined, depending on the technology and communication protocols used.

In operation 706, the device will communicate and connect with each ATD having the SU-ID until the correct ATD is found. As noted above, the device 200, utilizing the app and operating system will perform the scanning and connection to the ATDs in order to find ATDs having the SU-ID. If only one has a matching SU-ID, then the connection will proceed to auto linking 708. If more than one ATD has a matching SU-ID, the app on the device 200 will examine the complete serial number of the ATD to determine which ATD is the correct one.

In this example, it is determined that tracker 1 is one of the ATDs generating advertisement signal with an SU-ID that matches the SU-ID of tracker 1 in the user account of user A. The auto linking will then proceed in operation 708 when the device is linked to tracker 1. As noted above, the linking occurs automatically, and the operations performed between the device and the ATD to identify the correct ATD occur without user intervention or selection made by the user. The user simply logs in to the user account on the app of the device, and the device in the background will negotiate and identify the proper ATD to establish the auto-link.

Figure 7B:
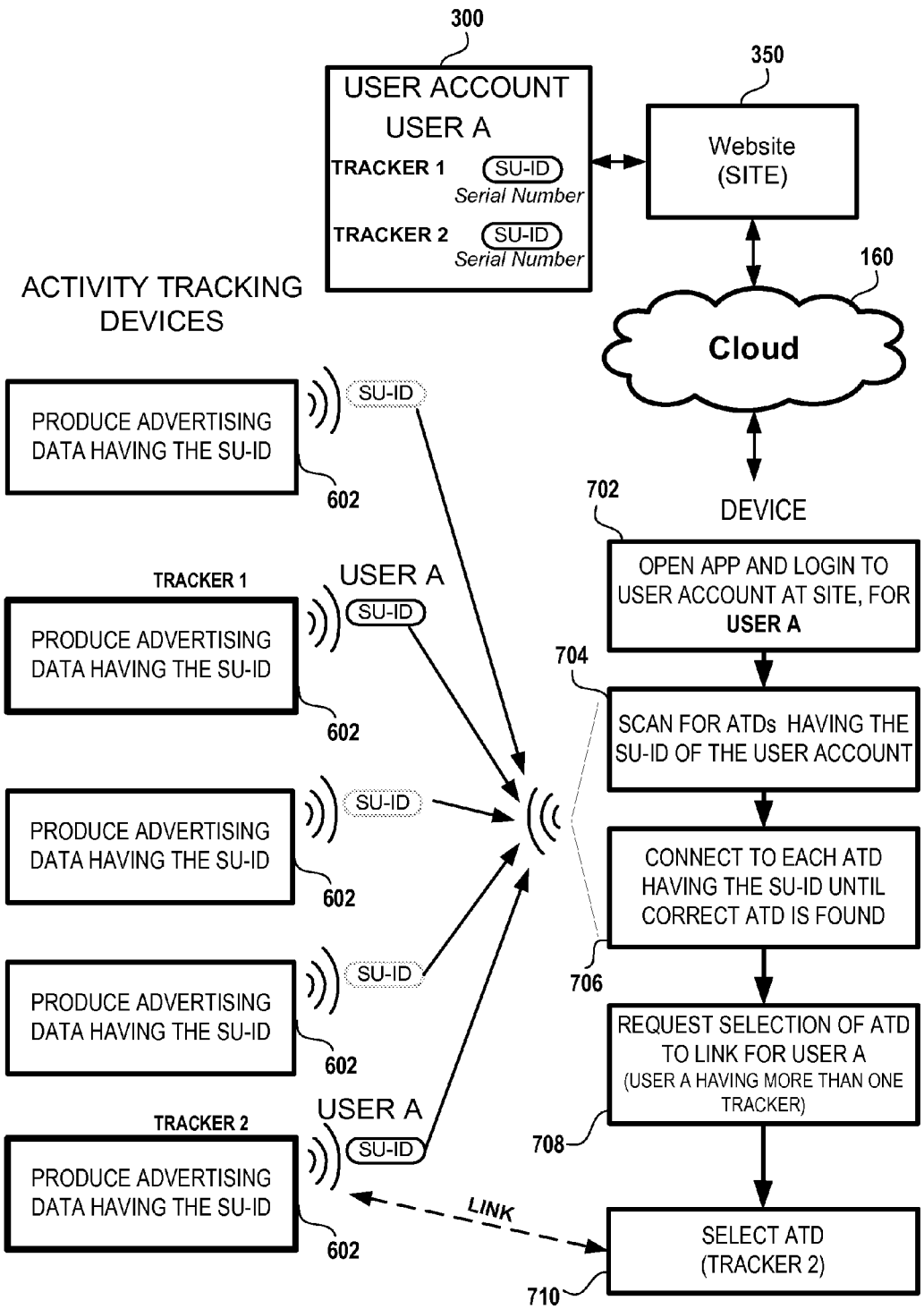
FIG. 7B illustrates an example where user A, in accordance with the user account, has two ATDs associated with the account (e.g., tracker 1 and tracker 2).

FIG. 7B illustrates an example where user A, in accordance with the user account 300, has two ATDs associated with the account (e.g., tracker 1 and tracker 2). For example, a plurality of ATDs at a particular location can be transmitting their advertisement messages with their respective SU-IDs. As in the embodiment of FIG. 7A, the device 702 will open the app and login to the user account at the site, for user A. In one embodiment, logging into the account can be automatic, if the user has saved the login credentials. In such a configuration, the user simply has to open the app, which automatically logs the user into his or her account.

The device in operations 704 and 706 will scan for ATDs having SU-IDs of the user account, and connecting each of the ATDs until the correct ATDs are found. In this example, more than one ATD has been found having SU-IDs that are assigned to User A's account. For this configuration, a message can be generated to the user on the device 200, to prompt selection of one of the ATD to link to at this particular time, as shown in operation 708. The user selects the link to tracker to in operation 710, which allows the device to auto-link with the tracker 2. In this configuration, the device has identified two trackers that belong to user account A. Although the user has selected to link with tracker 2, the user can be provided with an interface to toggle between linking with tracker 1, instead of tracker 2, or back to tracker 1. This provides for an efficient way for the device to connect to multiple trackers and access data or functionality of the trackers by way of the app of the device. In another embodiment, the device 200 can link to more than one device at the same time.

FIG. 8A illustrates an example where an ATD executes operations to enable the auto linking to occur, in one embodiment of the present invention. In operation 802, advertising data is generated by the ATD, including the SU-ID of the tracker.

In operation 804, the ATD will exchange communication with a device having the SU-ID. As noted above, the device will obtain the SU-ID from the site when the device opens and logs into the user account, which holds the serial number (and SU-ID) for that account. Thus, the tracker in operation 804 will be advertising the SU-ID, and the device will have knowledge of the SU-ID to identify the ATD for making the link. In operation 806, the tracker is linked to the device having the SU-ID that matches. Again, as noted above, if multiple ATDs have the same SU-ID, a further determination will be made to verify the matching ATD with complete serial number or parts of the serial number.

FIG. 8B illustrates an example where a device 200 can operate to establish a link with an ATD, in accordance with one embodiment of the present invention. In operation 808, the device will obtain the serial number for an ATD for a user account, when the device opens an application and logs into the user account. The device in operation 810 will scan for trackers advertising their SU-IDs. In operation 812, the device will identify the tracker having the SU-ID, which was obtained from the serial number.

In one embodiment, operation 813 is optionally performed if more than one ATD has the same SU-ID. In this operation, the full serial number may be used to correctly identify the ATD. In operation 814, the correct device will auto-link with the tracker having the matching SU-ID, provided no other trackers have the same SU-ID.

In an another embodiment, operation 813-1 is processed instead of operation 813. In operation 813-1, the ATD is correctly identified after the SU-ID has been determined to be a match. In this implementation, even if only one ATD with a matching SU-ID is found by the device 200, the ATD is verified to be the correct ATD that is associated with the user's account on the site 350. In one example configuration, the complete, full or part of the serial number of the ATD is compared to the serial number of the ATD. The ATD and the device 200 will communicate, wherein the ATD will provide the serial number to the device 200, and the device 200 can verify or confirm that the ATD with the matching SU-ID is the correct ATD. In an alternate embodiment, other data other than the serial number can be used to complete the verification. As noted above, the data can be pre-defined, pre-assigned, or randomly generated, depending on the implementation.

In one implementation, the following operations can be executed to first pair a tracker to the site, and then later use an app to automatically link to the tracker. For example, a user pairs a tracker to a site using a dongle or a device. The device, in one embodiment can be an iOS device. In this implementation, the dongle/iOS scans for available devices. The user pairs to one of the discovered devices. The tracker sends the site various information about the device. For example, the serial number may be sent. The serial number may have various components, such as date of manufacture, seconds from midnight on day of manufacture, location of manufacture, device type, etc. The SU-ID may be part of the serial number, such as bit data that defines the seconds from midnight on day of manufacture, for the ATD. The site receives the serial number and can derive the SU-ID from the serial number.

In this implementation, the SU-ID is a small part of the serial number. As an example only, it may be 16 bits that should be fairly distributed, as described above. Again, the SU-ID is not completely unique, but unique enough that iOS or code should only have to connect to a very small number of possible matches. The tracker can now advertise with the semi-unique ID (SU-ID).

From time to time, the user may open and log in to the mobile app (e.g., activity tracking app). The iOS app understands that a tracker has been paired but not linked. The iOS app scans for devices and checks for a correct semi-unique ID. It should be understood that scans are much less processor and power consuming intensive that a full connection. The iOS app connects to each tracker with the correct ID until it finds the correct one.

By using the SU-ID, the device can identify the appropriate tracker in the background without user intervention. This process makes it possible to save on processing power and/or power consumption by the ATD and device, (which avoids unneeded connections, to look for the right tracker). Also, by using a semi-unique ID, the advertising packet is small (e.g., in one example, 16 bits). A fully unique ID would be larger and would require more energy to continually broadcast, but it is possible to use a fully unique ID in an alternate embodiment.

Several advantages are possible, without limitation to others and by way of the various embodiments of the present invention. For instance, users no longer need to initiate the linking process. The app can ask the site if there is a tracker that should be linked and not draw very much extra power to scan for the tracker. Also, the app does not need to connect to every tracker to find the right tracker. Using a semi-unique ID will act to reduce the possible matches. The semi-unique ID (SU-ID) also allows for less data to be advertised than a fully unique ID which reduces power.

In one embodiment, if additional ATDs are added to a user account (e.g., paired to the site), the site can send the device a message or link that will allow selection or access to another ATD. For instance, the user may wish to link to one of the two or more ATDs that the user has added to his or her account. The user may select which ATD the user wishes to link to, after opening the site (e.g., by selecting one of the trackers on the site). The device 200 will then perform the background scanning of ATDs, and find the correct ATD with the matching SU-ID. Thus, the site can provide additional SU-IDs to the device, based on which trackers have been added (e.g., paired) to the site by users, to their respective user accounts. The site therefore sends the app information on what trackers are currently linked to the account and the additional tracker identifiers (e.g., SU-IDs). In this implementation, the trackers assume a slave role with the mobile app acting as a master.

In still another embodiment, the tracker can take the role of master and the mobile app can take the role of slave. In either configuration, the matching or finding of trackers uses identification of the SU-IDs, which are known to the site and the app on the device 200. In this manner, it is possible to scan for the correct ATD and complete the auto-linking in the background without or with minimal user intervention.

In one example where device 200 takes the role of a slave, the device 200 can be configured to broadcast or advertise identification data. The identification data that the device 200 broadcasts can be, for example, the serial number or SU-ID of the ATD that it wishes to connect with. In this configuration, the ATD can be placed in or configured to be in a mode enables scanning or discovery of the broadcasts or advertising data by device 200.

In another configuration, the ATD is configured with additional communication capability, to allow the ATD to communicate with the site 350. In one configuration, the ATD (e.g., having logic/circuitry) can communicate with the site directly using a wireless connection, such as cellular link, a WiFi link, Bluetooth link, etc. In another embodiment, the ATD can link to another device to enable communication to the site 350. For instance, the ATD can utilize the communication capabilities of a smartphone, which would enable the ATD to connect with the site 350.

In one configuration, the ATD can access the site 350 to obtain the serial numbers or SU-IDs of one or more tracker devices associated with a user/user account. For instance, a user can be wearing or carrying multiple tracker devices, and one ATD can be configured as the master that scans for other ATDs, which enables linking and collection of tracking data from the multiple devices. In one embodiment, data obtained from the various ATDs can be for the same metric or different metrics. In the case of the same collected metric, logic of the site 350 or the activity tracking application 202 of the device 200 can determine which data should be selected from each ATD. In the example of steps taken metric, it may be considered that ATD 1 has better or more accurate metric collection capabilities than ATD 2, and thus the steps taken metric of ATD 1 will be shown on the site. In other embodiments, the site and/or app on the mobile device can be provided with access to the complete metrics collected from all ATDs. In other embodiments, metrics from multiple ATDs will be synchronized or filtered based on priority rules that are accessed and implemented by logic of the site 350 and/or the app of device 200.

With the above configurations in mind, it should be understood that either the tracker or device 200 can take one the role of slave or master. In either role, the ability to scan for and identify devices or apps using a serial number or SU-ID can be used to reduce the number of devices/trackers that must be connected to when finding the correct device. As mentioned above, it should be understood that the serial number is just one example of data that can be used to identify a tracker or device, and other data can also be used. The data used for identification can be assigned based on any metric or logic, or can be generated using random number or data generation, etc. The SU-ID can therefore be generated or derived from any type of data, not just a serial number. Once an SU-ID is found on an advertising/broadcasting device, other data can be queried to confirm that the device (e.g., tracker device or device 200) is the correct device (e.g., depending on which is the slave and which is the master).

In one configuration, an activity tracker is paired to a user's web based account. A client application is capable of being logged into the same web based account. The client application would like to easily get data on demand from the paired activity tracker. In this configuration, efficient establishment of some kind of persistent bond between itself and the activity tracker is needed. This bond may be a Bluetooth Pairing or simply a record of some other persistent identifier such a MAC (media access controller) address/number or device UUID.

In one example, the tracker will broadcast the semi-unique identifier, which serves as a hint. If the semi-unique identifier matches, then it is probably the correct tracker. The client application will then connect to the tracker and query the full device identifier. In this example, after verifying the full device identifier, a persistent bond between activity tracker and client application is established.

In an alternate configuration, every tracker has a unique identifier that may be requested once connected to. This identifier may be is too long to broadcast in advertisements. Thus, in this configuration, a client application must connect to every activity tracker it finds until it finds one with the correct unique identifier.

Figure 9:
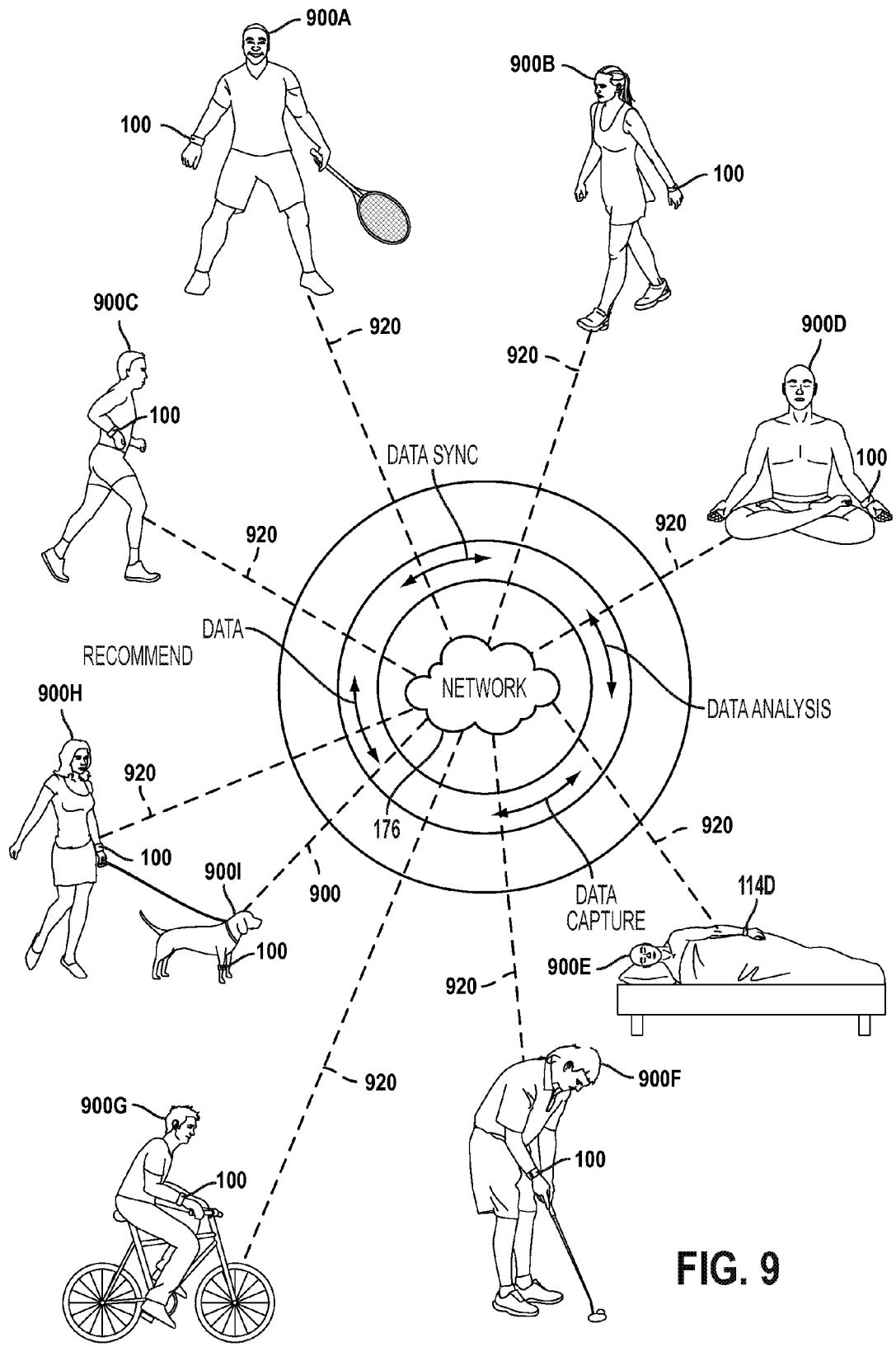
FIG. 9 illustrates an example where various types of activities of users can be captured or collected by activity tracking devices, in accordance with various embodiments of the present invention.

FIG. 9 illustrates an example where various types of activities of users 900A-900I can be captured by activity tracking devices 100, in accordance with one embodiment of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the user's account, which can be managed by an activity management application on the server. The activity management application can provide access to the user's account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g., smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the user's smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the user's device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

In yet another embodiment, the device can include one or more accelerometers. In one specific example, the device can include a 3-axis accelerometer. On still another embodiment, a 3-axis accelerometer can be replaced with or replicated by use of separate accelerometers (e.g., 3 accelerometers) positioned orthogonally to each other.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method, comprising,
    scanning, by an activity tracking device, for a semi-unique identifier broadcasted by a device;
    connecting the device with the activity tracking device after the semi-unique identifier is found to be of the device by the activity tracking device, the activity tracking device configured to query the device to obtain a device identification (ID) of the device;
    linking the device to the activity tracking device when the device ID of the device matches a copy of the device ID stored in the activity tracking device; and
    automatically processing the connecting to then process the linking without requiring user input, the activity tracking device being configured to store additional device IDs associated with devices that have been pre-defined to link to the activity tracking device, the devices being pre-defined to link to the activity tracking device based on pre-made pairings of the devices to the activity tracking device, as defined in a user account, and the user account maintaining a current association of the activity tracking device to one or more devices, the method being executed by a processor.

2. The method of claim 1, wherein the scanning and connecting is repeated for other devices having the semi-unique identifier until the match is made between the device ID and the copy of the device ID.

3. The method of claim 1, wherein when the linking is complete, data captured by the activity tracking device is transferred to the device for display on a screen of the display.

4. The method of claim 1, wherein the user account is associated with a website and manages a current association of the activity tracking device to the device.

5. The method of claim 4, wherein the user account is accessible by one or both of the activity tracking device and the device, the website being executed by a server.

6. The method of claim 1, wherein the device ID,
    is a unique identifier; or
    is a semi-unique identifier; or
    is an identifier that is part of the device ID; or
    is a randomly generated number that is pre-associated to the device ID.

7. The method of claim 1, wherein broadcasting of the semi-unique identifier includes transmitting data by a wireless communication device of the device.

8. The method of claim 7, wherein the wireless communication device enables at least part of the broadcasting using a Bluetooth low energy (BT LE) protocol, or a Bluetooth (BT) protocol, or a WiFi protocol, or a cellular protocol, or a radio transmission protocol, or a combination of two or more thereof.

9. The method of claim 1, wherein the user account is managed by a website server.

10. The method of claim 9, wherein the semi-unique identifier is bit data transferred in payload of an advertising packet, the advertising packet being broadcast by the device.

11. A tracking device configured for capture of activity for a user, comprising,
a housing;
a sensor disposed in the housing to capture motion data associated with activity of the user;
memory for storing the captured motion data and a device identification (ID) of a device that the tracking device is able to initiate connection and link therewith; and
a processor configured to scan for a semi-unique identifier broadcasted by the device, the processor enabling connection with the device with the tracking device after the semi-unique identifier is found to be of the device by the tracking device, the tracking device configured to query the device to obtain a device identification (ID) of the device, the processor linking the device to the tracking device when the device ID of the device matches a copy of the device ID stored in the memory of the tracking device,
the device being a portable computing device, the device configured for access with an activity management server over the Internet, the activity management server having a user account in which the tracking device is associated, and the user account enabling association of additional tracking devices and additional portable computing devices, and their associations for enabling respective links.

12. The tracking device of claim 11, wherein the housing is part of a wearable wrist attachable structure, or an attachable structure that can be carried or worn by the user, and the wearable wrist attachable structure is defined at least partially from a plastic material, the housing further including a battery for providing power to the tracking device.

13. The tracking device of claim 11, wherein the housing further includes wireless communication logic for enabling wireless connections.

14. A tracking device configured for capture of activity for a user, comprising,
a housing;
a sensor disposed in the housing to capture motion data associated with activity of the user;
memory for storing the captured motion data and a device identification (ID) of a device that the tracking device is able to initiate connection and link therewith; and
a processor configured to scan for a semi-unique identifier broadcasted by the device, the processor enabling connection with the device with the tracking device after the semi-unique identifier is found to be of the device by the tracking device, the tracking device configured to query the device to obtain a device identification (ID) of the device, the processor linking the device to the tracking device when the device ID of the device matches a copy of the device ID stored in the memory of the tracking device, the processor of the tracking device including circuits, and at least one of said circuits including a firmware circuit having program instructions to enable the linking and then enabling transfer of data collected by the tracking device to the device for display on a screen of the device.

15. Computer readable medium having program instructions for enabling tracking devices to automatically link with devices, the computer readable medium, comprising,
program instructions for scanning, by an activity tracking device, for a semi-unique identifier broadcasted by a device;
program instructions for connecting the device with the activity tracking device after the semi-unique identifier is found to be of the device by the activity tracking device, the activity tracking device configured to query the device to obtain a device identification (ID) of the device; and
program instructions for linking the device to the activity tracking device when the device ID of the device matches a copy of the device ID stored in the activity tracking device; and
program instructions for automatically processing the connecting to then process the linking without requiring user input, the activity tracking device being configured to store additional device IDs associated with devices that have been pre-defined to link to the activity tracking device, the devices being pre-defined to link to the activity tracking device based on pre-made pairings of the devices to the activity tracking device as defined in a user account, and the user account maintaining a current association of the activity tracking device to one or more devices.

16. An activity tracking device configured for capture of activity for a user, comprising,
a housing;
a sensor disposed in the housing to capture motion data associated with activity of the user;
memory for storing the captured motion data and a copy of a device identification (ID) of a device that the activity tracking device is able to initiate connection and link therewith; and
a processor configured to scan for a semi-unique identifier broadcasted by a device, connect the device with the activity tracking device after the semi-unique identifier is found to be of the device by the activity tracking device, the processor is configured to query the device to obtain the device identification (ID) of the device, link the device to the activity tracking device when the device ID of the device matches the copy of the device ID stored in the memory of the activity tracking device, the processor automatically processing the connecting to then process the linking without requiring user input, the activity tracking device being configured to store additional device IDs associated with devices that have been pre-defined to link to the activity tracking device, the devices being pre-defined to link to the activity tracking device based on pre-made pairings of the devices to the activity tracking device, as defined in a user account, and the user account maintaining a current association of the activity tracking device to one or more devices.

17. A method, comprising,
scanning, by an activity tracking device, for a semi-unique identifier broadcasted by a device;
connecting the device with the activity tracking device after the semi-unique identifier is found to be of the device by the activity tracking device, the activity tracking device configured to query the device to obtain a device identification (ID) of the device;

linking the device to the activity tracking device when the device ID of the device matches a copy of the device ID stored in the activity tracking device, the device being a portable computing device, the device configured for access with an activity management server over the Internet, the activity management server having a user account in which the activity tracking device is associated, and the user account enabling association of additional activity tracking devices and additional portable computing devices, and their associations for enabling respective linking.

18. Computer readable media having non-transitory program instructions, comprising, program instructions for scanning, by an activity tracking device, for a semi-unique identifier broadcasted by a device;

program instructions for connecting the device with the activity tracking device after the semi-unique identifier is found to be of the device by the activity tracking device, the activity tracking device configured to query the device to obtain a device identification (ID) of the device;

program instructions for linking the device to the activity tracking device when the device ID of the device matches a copy of the device ID stored in the activity tracking device, the device being a portable computing device, the device configured for access with an activity management server over the Internet, the activity management server having a user account in which the activity tracking device is associated, and the user account enabling association of additional activity tracking devices and additional portable computing devices, and their associations for enabling respective linking.

19. A method, comprising, scanning, by an activity tracking device, for a semi-unique identifier broadcasted by a device;

connecting the device with the activity tracking device after the semi-unique identifier is found to be of the device by the activity tracking device, the activity tracking device configured to query the device to obtain a device identification (ID) of the device;

linking the device to the activity tracking device when the device ID of the device matches a copy of the device ID stored in the activity tracking device;

wherein a processor of the activity tracking device includes circuits, and at least one of said circuits include a firmware circuit having program instructions to enable the linking and then enabling transfer of data collected by the activity tracking device to the device for display on a screen of the device.

20. Computer readable media having non-transitory program instructions, comprising, program instructions for scanning, by an activity tracking device, for a semi-unique identifier broadcasted by a device;

program instructions for connecting the device with the activity tracking device after the semi-unique identifier is found to be of the device by the activity tracking device, the activity tracking device configured to query the device to obtain a device identification (ID) of the device;

program instructions for linking the device to the activity tracking device when the device ID of the device matches a copy of the device ID stored in the activity tracking device, the activity tracking device having circuits, and at least one of said circuits include a firmware circuit having program instructions to enable the linking and then enabling transfer of data collected by the activity tracking device to the device for display on a screen of the device.

* * * * *